United States Patent [19]
Voorberg

[11] Patent Number: 5,869,292
[45] Date of Patent: Feb. 9, 1999

[54] HYBRID PROTEINS WITH MODIFIED ACTIVITY

[75] Inventor: Johannes J. Voorberg, Assendelft, Netherlands

[73] Assignee: Immuno AG, Vienna, Austria

[21] Appl. No.: 882,083

[22] Filed: Jun. 25, 1997

Related U.S. Application Data

[62] Division of Ser. No. 558,107, Nov. 13, 1995.

[51] Int. Cl.[6] ........................... C12P 21/04; C12P 21/06; A61K 35/14; A61K 38/00
[52] U.S. Cl. ..................... 435/69.6; 435/69.1; 435/69.7; 530/383; 530/324; 530/350; 536/23.5
[58] Field of Search ................................. 435/69.1, 69.6, 435/69.7; 530/383, 350; 536/23.5

[56] References Cited

U.S. PATENT DOCUMENTS

| | | | |
|---|---|---|---|
| 4,868,112 | 9/1989 | Toole | 514/8 |
| 5,286,487 | 2/1994 | Vallee et al. | 424/94.6 |
| 5,358,932 | 10/1994 | Foster et al. | 514/12 |
| 5,364,771 | 11/1994 | Lollar et al. | 435/69.1 |

FOREIGN PATENT DOCUMENTS

| | | |
|---|---|---|
| 150 735 | 8/1985 | European Pat. Off. . |
| 160 457 | 11/1985 | European Pat. Off. . |
| 253 455 | 1/1988 | European Pat. Off. . |
| 294 910 | 12/1988 | European Pat. Off. . |
| 296 413 | 12/1988 | European Pat. Off. . |
| 352 119 | 1/1990 | European Pat. Off. . |
| WO 85/01961 | 5/1985 | WIPO . |
| 146 903 | 7/1985 | WIPO . |
| WO 86/06101 | 10/1986 | WIPO . |
| WO 88/03926 | 6/1988 | WIPO . |
| WO 88/08451 | 11/1988 | WIPO . |
| WO 89/02922 | 4/1989 | WIPO . |
| WO 90/11092 | 10/1990 | WIPO . |
| WO 91/05048 | 4/1991 | WIPO . |
| WO 93/09236 | 5/1993 | WIPO . |
| WO 94/11013 | 5/1994 | WIPO . |
| WO 94/11503 | 5/1994 | WIPO . |
| WO 95/18827 | 7/1995 | WIPO . |
| WO 95/18828 | 7/1995 | WIPO . |
| WO 95/18829 | 7/1995 | WIPO . |

OTHER PUBLICATIONS

Aledort, Sem.Hematol. 30(2): 7–9 (1993).
Bode et al., EMBO J. 8(11): 3467–75 (1989).
Brackman et al., Lancet 2: 933 (1977).
Chibber et al., Biochemistry 24: 3429–34 (1985).
Coughlin et al., J. Clin. Invest. 89:351–55 (1992).
Culver et al., Science 256: 1550–52 (1992).
Davie et al., Science 145: 1310–12 (1964).
Davie et al., Biochem. 30(43): 10363–70 (1991).
Eaton et al., Biochemistry 25(26): 8343–47 (1986).
Eaton et al., Biochem. 25: 505–12 (1986).
Esmon, Thromb. Haemost. 70(1): 29–35 (1993).
Fay et al. Thromb. Haemost. 70: 63–67 (1993).
Foss et al., Blood 84(6): 1765–74 (1994).
Gailani et al., Science 253: 909–12 (1991).
Graham et al. Virology 52: 456–67 (1997).
Grütter et al. EMBO J. 9(8): 2361–65 (1990).
Hortin et al., Biochem. Biophys. Res. Commun. 169(2): 437–442 (1990).
Huber et al., Biochem. 28(23): 8951–66 (1989).
Jackson et al., Ann. Rev. Biochem. 49: 765 (1980).
Jesty, Haemostasis 21: 208–18 (1991).
Johnson et al., "Peptide Turn Mimetics" in Biotechnology and Pharmacy.
Kane et al. Blood 71(3): 539–55 (1988).
Kreitman et al., Biochemistry 33: 11637–44 (1994).
Lenting et al., J. Biol. Chem. 269: 7150–55 (1994).
Leyte et al., J. Biol. Chem. 266(2): 740–46 (1991).
Leyte et al., J. Biochem. 263: 187–94 (1989).
Liu et al., J. Biol. Chem. 266(26): 16977–80 (1991).
Lollar et al., J. Biol. Chem. 263(21): 10451–55 (1988).
Lollar et al., Biochemistry 28: 666–74 (1989).
MacFarlane, Nature 202: 498–99 (1964).
Mann et al. Blood 76(1): 1–16 (1990).
Mathews et al., Biochemistry 33: 6322–79 (1994).
Mertens et al., Brit. J. Haematol. 85: 1–10 (1993).
Mertens et al., J. Biochem. 223: 599–605 (1984).
Michnick et al., J. Biol. Chem. 269(31): 20095–102 (1994).
Mikkelsen et al., Biochemistry 30: 1533–37 (1991).
Neuenschwander et al., Analyt. Biochem. 184: 347–52 (1990).
Pittman et al., Biochemistry 31(13): 3315–25 (1992).
Rosenberg et al., Human Gene Therapy 3: 57–75 (1992).
Rydel et al., Science 249: 277–80 (1990).
Saragovi et al., Science 253: 792–95 (1991).
Sarver et al., DNA 6(6):553–64 (1987).
Skrzypczak–Jankun et al., J. Mol. Biol. 206: 755–57 (1989).
Stubbs et al., Thromb. Res. 69: 1–58 (1993).
te Riele et al., Nature 348: 649–51 (1990).
Toole et al., Proc. Nat'l Acad. Sci. USA 83: 5939–42 (1986).
Tsiang et al., Biochemistry 29: 10602–12 (1990).
Van Deerlin et al., J. Biol. Chem. 266(30): 20223–31 (1991).
Vu et al., Nature 353: 674–77 (1991).
Yelton et al., Ann. Rev. Biochem. 50: 657–680 (1981).
Voorberg et al. Journal of Biological Chemistry 271(35): 20985–20988 (1996).
Mertens et al. British Journal of Haematology 85: 133–142 (1993).
Donath et al. Activation and Limited Proteolysis of Human Blood Coagulation Factor VIII, pp. 33–48 (1995).

Primary Examiner—Robert A. Wax
Assistant Examiner—Elizabeth Slobodyansky
Attorney, Agent, or Firm—Foley & Lardner

[57] ABSTRACT

Hybrid proteins which affect blood coagulation comprise a region from a donor anticoagulant or antithrombotic protein, and the resulting hybrid protein has a modified biological activity. Information concerning the hybrid proteins implicates DNA sequences encoding the proteins and hosts, including transgenic animals, that possess these DNA sequences; antibodies directed against hybrid proteins; methods of modifying the properties of proteins; and treatment methods employing hybrid proteins.

2 Claims, 20 Drawing Sheets

FIG. 7A

```
TCGACCTCCA GTTGAACATT TGTAGCAAGC CACC ATG GAA ATA GAG CTC TCC          52
                                     Met Glu Ile Glu Leu Ser
                                      1               5

ACC TGC TTC TTT CTG TGC CTT TTG CGA TTC TGC TTT AGT GCC ACC AGA       100
Thr Cys Phe Phe Leu Cys Leu Leu Arg Phe Cys Phe Ser Ala Thr Arg
            10                  15                  20

AGA TAC TAC CTG GGT GCA GTG GAA CTG TCA TGG GAC TAT ATG CAA AGT       148
Arg Tyr Tyr Leu Gly Ala Val Glu Leu Ser Trp Asp Tyr Met Gln Ser
        25                  30                  35

GAT CTC GGT GAG CTG CCT GTG GAC GCA AGA TTT CCT AGA GTG CCA           196
Asp Leu Gly Glu Leu Pro Val Asp Ala Arg Phe Pro Pro Arg Val Pro
    40                  45                  50

AAA TCT TTT CCA TTC AAC ACC TCA GTC GTG TAC AAA AAG ACT CTG TTT       244
Lys Ser Phe Pro Phe Asn Thr Ser Val Val Tyr Lys Lys Thr Leu Phe
 55                  60                  65                  70

GTA GAA TTC ACG GAT CAC CTT TTC AAC ATC GCT AAG CCA AGG CCA CCC       292
Val Glu Phe Thr Asp His Leu Phe Asn Ile Ala Lys Pro Arg Pro Pro
            75                  80                  85

TGG ATG GGT CTG CTA GGT CCT ACC ATC CAG GCT GAG GTT TAT GAT ACA       340
Trp Met Gly Leu Leu Gly Pro Thr Ile Gln Ala Glu Val Tyr Asp Thr
        90                  95                 100

GTG GTC ATT ACA CTT AAG AAC ATG GCT TCC CAT CCT GTC AGT CTT CAT       388
Val Val Ile Thr Leu Lys Asn Met Ala Ser His Pro Val Ser Leu His
    105                 110                 115
```

FIG. 7B

```
GCT GTT GGT GTA TCC TAC TGG AAA GCT TCT GAG GGA GCT GAA TAT GAT    436
Ala Val Gly Val Ser Tyr Trp Lys Ala Ser Glu Gly Ala Glu Tyr Asp
120                 125                 130

GAT CAG ACC AGT CAA AGG GAG AAA GAT GAT AAA GTC TTC CCT GGT         484
Asp Gln Thr Ser Gln Arg Glu Lys Asp Asp Lys Val Phe Pro Gly
135                 140                 145                 150

GGA AGC CAT ACA TAT GTC TGG CAG GTC CTG AAA GAG AAT GGT CCA ATG     532
Gly Ser His Thr Tyr Val Trp Gln Val Leu Lys Glu Asn Gly Pro Met
155                 160                 165

GCC TCT GAC CCA CTG TGC CTT TCT CAT GTG GAC                         580
Ala Ser Asp Pro Leu Cys Leu Ser His Val Asp
170                 175                 180

CTG GTA AAA GAC TTG AAT TCA GGC CTC ATT GGA GCC CTA CTA TGT         628
Leu Val Lys Asp Leu Asn Ser Gly Leu Ile Gly Ala Leu Leu Cys
185                 190                 195

AGA GAA GGG AGT CTG GCC AAG GAA AAG ACA CAG ACC TTG CAC AAA TTT     676
Arg Glu Gly Ser Leu Ala Lys Glu Lys Thr Gln Thr Leu His Lys Phe
200                 205                 210

ATA CTA CTT TTT GCT GTA TTT GAT GAA GGG AAA AGT TGG CAC TCA GAA     724
Ile Leu Leu Phe Ala Val Phe Asp Glu Gly Lys Ser Trp His Ser Glu
215                 220                 225                 230
```

FIG. 7C

```
ACA AAG AAC TCC TTG ATG CAG GAT AGG GAT GCT GCA TCT GCT CGG GCC    772
Thr Lys Asn Ser Leu Met Gln Asp Arg Asp Ala Ala Ser Ala Arg Ala
            235                 240                 245

TGG CCT AAA ATG CAC ACA GTC AAT GGT TAT GTA AAC AGG TCT CTG CCA    820
Trp Pro Lys Met His Thr Val Asn Gly Tyr Val Asn Arg Ser Leu Pro
            250                 255                 260

GGT CTG ATT GGA TGC CAC AGG AAA TCA GTC TAT TGG CAT GTG ATT GGA    868
Gly Leu Ile Gly Cys His Arg Lys Ser Val Tyr Trp His Val Ile Gly
            265                 270                 275

ATG GGC ACC ACT CCT GAA GTG CAC CAT CGC CAG GCG TCC TTG GAA ATC CTC CCA ATA    916
Met Gly Thr Thr Pro Glu Val His Ser Arg Gln Ala Ser Val His Thr
280                 285                 290

TTT CTT GTG AGG AAC CAT CGC CAG GCG TCC TTG GAA ATC TCG CCA ATA    964
Phe Leu Val Arg Asn His Arg Gln Ala Ser Leu Glu Ile Ser Pro Ile
295                 300                 305                 310

ACT TTC ACT GCT CAA ACA CTC TTG ATG GAC CTT GGA CAG TTT CTA       1012
Thr Phe Thr Ala Gln Thr Leu Leu Met Asp Leu Gly Gln Phe Leu
            315                 320                 325

CTG TTT TGT CAT ATC TCT TCC CAC CAA CAT GGC ATG GAA GCT TAT       1060
Leu Phe Cys His Ile Ser Ser His Gln His Gly Met Glu Ala Tyr
            330                 335                 340

GTC AAA GTA GAC AGC TGT CCA GAG CCC CAA CTA CGA ATG AAA AAT       1108
Val Lys Val Asp Ser Cys Pro Glu Pro Gln Leu Arg Met Lys Asn
            345                 350                 355
```

FIG. 7D

```
AAT GAA GCG GAA GAC TAT GAT GAT CTT ACT GAT TCT GAA ATG                1156
Asn Glu Ala Glu Asp Tyr Asp Asp Leu Thr Asp Ser Glu Met
360             365             370

GAT GTG GTC AGG TTT GAT GAC AAC TCT CCT TCC TTT ATC CAA ATT            1204
Asp Val Val Arg Phe Asp Asp Asn Ser Pro Ser Phe Ile Gln Ile
375             380             385             390

CGC TCA GTT GCC AAG CAT CCT AAA ACT GGT GTA CAT TAC ATT GCT            1252
Arg Ser Val Ala Lys His Pro Lys Thr Val His Tyr Ile Ala
395             400             405

GCT GAA GAG GAC TAT TGG GAC TAT GCT CCC TTA GTC CTC GCC CCC GAT        1300
Ala Glu Glu Asp Tyr Trp Asp Tyr Ala Pro Leu Val Leu Ala Pro Asp
410             415             420

GAC AGA AGT TAT AAA AGT CAA TAT TTG AAC AAT GGC CCT CAG CGG ATT        1348
Asp Arg Ser Tyr Lys Ser Gln Tyr Leu Asn Asn Gly Pro Gln Arg Ile
425             430             435

GGT AGG AAG TAC AAA AAA GTC CGA TTT ATG GCA TAC ACA GAT GAA ACC        1396
Gly Arg Lys Tyr Lys Lys Val Arg Phe Met Ala Tyr Thr Asp Glu Thr
440             445             450

TTT AAG ACT CGT GAA GCT ATT CAG CAT GAA TCA GGA ATC TTG GGA CCT        1444
Phe Lys Thr Arg Glu Ala Ile Gln His Glu Ser Gly Ile Leu Gly Pro
455             460             465             470

TTA CTT TAT GGG GAA GTT GGA GAC ACA CTG TTG ATT ATA TTT AAG AAT        1492
Leu Leu Tyr Gly Glu Val Gly Asp Thr Leu Leu Ile Ile Phe Lys Asn
475             480             485
```

FIG. 7E

```
CAA GCA AGC AGA CCA TAT AAC ATC TAC CCT CAC GGA ATC ACT GAT GTC        1540
Gln Ala Ser Arg Pro Tyr Asn Ile Tyr Pro His Gly Ile Thr Asp Val
        490                 495                 500

CGT CCT TTG TAT TCA AGG AGA TTA CCA AAA GGT GTA AAA CAT TTG AAG        1588
Arg Pro Leu Tyr Ser Arg Arg Leu Pro Lys Gly Val Lys His Leu Lys
        505                 510                 515

GAT TTT CCA ATT CTG CCA GGA GAA ATA TTC AAA TAT AAA TGG ACA GTG        1636
Asp Phe Pro Ile Leu Pro Gly Glu Ile Phe Lys Tyr Lys Trp Thr Val
        520                 525                 530

ACT GTA GAA GAT GGG CCA ACT AAA TCA GAT CCT CGG TGC CTG ACC CGC        1684
Thr Val Glu Asp Gly Pro Thr Lys Ser Asp Pro Arg Cys Leu Thr Arg
        535                 540                 545                 550

TAT TAC TCT AGT TTC GTT AAT ATG GAG AGA GAT CTA GCT TCA GGA CTC        1732
Tyr Tyr Ser Ser Phe Val Asn Met Glu Arg Asp Leu Ala Ser Gly Leu
        555                 560                 565

ATT GGC CCT CTC ATC TGC TAC AAA GAA TCT GTA GAT CAA AGA GGA            1780
Ile Gly Pro Leu Ile Cys Tyr Lys Glu Ser Val Asp Gln Arg Gly
        570                 575                 580

AAC CAG ATA ATG TCA GAC AAG AGG AAT GTC ATC CTG TTT TCT GTA TTT        1828
Asn Gln Ile Met Ser Asp Lys Arg Asn Val Ile Leu Phe Ser Val Phe
        585                 590                 595

GAT GAG AAC CGA AGC TGG TAC CTC ACA GAG AAT ATA CAA CGC TTT CTC        1876
Asp Glu Asn Arg Ser Trp Tyr Leu Thr Glu Asn Ile Gln Arg Phe Leu
        600                 605                 610
```

FIG. 7F

| | | | | | | | | | | | | | | | | |
|---|---|---|---|---|---|---|---|---|---|---|---|---|---|---|---|---|
| CCC | AAT | CCA | GCT | GGA | GTG | CAG | CTT | GAG | GAT | CCA | GAG | TTC | CAA | GCC | TCC | 1924 |
| Pro | Asn | Pro | Ala | Gly | Val | Gln | Leu | Glu | Asp | Pro | Glu | Phe | Gln | Ala | Ser | |
| 615 | | | | | 620 | | | | | 625 | | | | | 630 | |
| AAC | ATC | ATG | CAC | AGC | ATC | AAT | GGC | TAT | GTT | TTT | GAT | AGT | TTG | CAG | TTG | 1972 |
| Asn | Ile | Met | His | Ser | Ile | Asn | Gly | Tyr | Val | Phe | Asp | Ser | Leu | Gln | Leu | |
| | | | | 635 | | | | | 640 | | | | | 645 | | |
| TCA | GTT | TGT | TTG | CAT | GAG | GTG | GCA | TAC | ATT | CTA | AGC | ATT | GGA | 2020 |
| Ser | Val | Cys | Leu | His | Glu | Val | Ala | Tyr | Ile | Leu | Ser | Ile | Gly | |
| | 650 | | | | | 655 | | | | | 660 | | | | | |
| GCA | CAG | ACT | GAC | TTC | CTT | TCT | GTC | TTC | TTC | TCT | GGA | TAT | ACC | TTC | AAA | 2068 |
| Ala | Gln | Thr | Asp | Phe | Leu | Ser | Val | Phe | Phe | Ser | Gly | Tyr | Thr | Phe | Lys | |
| 665 | | | | | 670 | | | | | 675 | | | | | | |
| CAC | AAA | ATG | GTC | TAT | GAA | GAC | ACA | CTC | ACC | CTA | TTC | CCA | TTC | TCA | GGA | 2116 |
| His | Lys | Met | Val | Tyr | Glu | Asp | Thr | Leu | Thr | Leu | Phe | Pro | Phe | Ser | Gly | |
| 680 | | | | | 685 | | | | | 690 | | | | | | |
| GAA | ACT | GTC | TTC | ATG | TCG | ATG | GAA | AAC | CCA | GGT | CTA | TGG | ATT | CTG | GGG | 2164 |
| Glu | Thr | Val | Phe | Met | Ser | Met | Glu | Asn | Pro | Gly | Leu | Trp | Ile | Leu | Gly | |
| 695 | | | | | 700 | | | | | 705 | | | | | 710 | |
| TGC | CAC | AAC | TCA | GAC | TTT | CGG | AAC | AGA | GGC | ATG | ACC | GCC | TTA | CTG | AAG | 2212 |
| Cys | His | Asn | Ser | Asp | Phe | Arg | Asn | Arg | Gly | Met | Thr | Ala | Leu | Leu | Lys | |
| | | | | 715 | | | | | 720 | | | | | 725 | | |
| GTT | TCT | AGT | TGT | CCA | GAG | GGG | GAG | GAC | GAC | TAT | CTG | GAC | 2260 |
| Val | Ser | Ser | Cys | Ile | Pro | Glu | Gly | Glu | Asp | Asp | Tyr | Leu | Asp | |
| 730 | | | | | 735 | | | | | 740 | | | | |

FIG. 7G

```
CTG GAG AAG ATA TTC AGT GAA GAC GAC TAC ATC GAC ATC GTC GAC    2308
Leu Glu Lys Ile Phe Ser Glu Asp Asp Tyr Ile Asp Ile Val Asp
            745                 750                 755

AGT CTG ATT GAA CCA AGA AGC TTC TCC CAG AAT TCA AGA CAC CCT AGC   2356
Ser Leu Ile Glu Pro Arg Ser Phe Ser Gln Asn Ser Arg His Pro Ser
        760                 765                 770

ACT AGG CAA AAG CAA TTT AAT GCC ACC ACA ATT CCA GAA AAT GAC ATA   2404
Thr Arg Gln Lys Gln Phe Asn Ala Thr Thr Ile Pro Glu Asn Asp Ile
    775                 780                 785                 790

GAG AAG ACT GAC CCT TGG TTT GCA CAC AGA ACA CCT AAA ATA           2452
Glu Lys Thr Asp Pro Trp Phe Ala His Arg Thr Pro Met Pro Lys Ile
            795                 800                 805

CAA AAT GTC TCC TCT AGT GAT TTG ATG CTC TTG CGA CAG AGT CCT       2500
Gln Asn Val Ser Ser Ser Asp Leu Met Leu Leu Arg Gln Ser Pro
        810                 815                 820

ACT CCA CAT GGG CTA TCC TTA TCT GAT CTC CAA GAA GCC AAA TAT GAG   2548
Thr Pro His Gly Leu Ser Leu Ser Asp Leu Gln Glu Ala Lys Tyr Glu
    825                 830                 835

ACT TTT TCT GAT GAT CCA TCA CCT GGA GCA ATA GAC AGT AAT AAC AGC   2596
Thr Phe Ser Asp Asp Pro Ser Pro Gly Ala Ile Asp Ser Asn Asn Ser
        840                 845                 850

CTG TCT GAA ATG ACA CAC TTC AGG CCA CAG CTC CAT CAC AGT GGG GAC   2644
Leu Ser Glu Met Thr His Phe Arg Pro Gln Leu His His Ser Gly Asp
    855                 860                 865                 870
```

FIG. 7H

```
ATG GTA TTT ACC CCT GAG TCA GGC CTC CAA TTA AGA TTA AAT GAG AAA    2692
Met Val Phe Thr Pro Glu Ser Gly Leu Gln Leu Arg Leu Asn Glu Lys
                875                 880                 885

CTG GGG ACA ACT GCA GAT CCT CTT GCT CTT TGG GAT AAC CAC TAT GGT ACT    2740
Leu Gly Thr Thr Ala Asp Pro Leu Ala Leu Trp Asp Asn His Tyr Gly Thr
            890                 895                 900

CAG ATA CCA AAA GAA GAG TGG AAA GAG TCC CAA GAG AAG TCA CCA GAA AAA    2788
Gln Ile Pro Lys Glu Glu Trp Lys Glu Ser Gln Glu Lys Ser Pro Glu Lys
            905                 910                 915

ACA GCT TTT AAG AAA AAG GAT ACC ATT TTG TCC CTG AAC GCT TGT GAA    2836
Thr Ala Phe Lys Lys Lys Asp Thr Ile Leu Ser Leu Asn Ala Cys Glu
                920                 925                 930

AGC AAT CAT GCA ATA GCA ATA AAT GAG GGA GGT CAA AAT GAG CCC GAA    2884
Ser Asn His Ala Ile Ala Ile Asn Glu Gly Gly Gln Asn Lys Pro Glu
        935                 940                 945                 950

ATA GAA GTC ACC TGG GCA AAG CAA GGT AGG ACT GAA AGG CTG TGC TCT    2932
Ile Glu Val Thr Trp Ala Lys Gln Gly Arg Thr Glu Arg Leu Cys Ser
            955                 960                 965

CAA AAC CCA CCA CGC CAT CAA CGG GAA ATA ACT CGT ACT    2980
Gln Asn Pro Pro Val Leu Lys Arg His Gln Arg Glu Ile Thr Arg Thr
            970                 975                 980

ACT CTT CAG TCA GAT CAA GAG GAA ATT GAC TAT GAT GAT ACC ATA TCA    3028
Thr Leu Gln Ser Asp Gln Glu Glu Ile Asp Tyr Asp Asp Thr Ile Ser
        985                 990                 995
```

FIG. 7I

```
GTT GAA ATG AAG AAG GAA GAT TTT GAC ATT TAT GAT GAG GAT GAA AAT    3076
Val Glu Met Lys Lys Glu Asp Phe Asp Ile Tyr Asp Glu Asp Glu Asn
1000                          1005                    1010

CAG AGC CCC CGC AGC TTT CAA AAG ACA CGA CAC TAT TTT ATT GCT        3124
Gln Ser Pro Arg Ser Phe Gln Lys Thr Arg His Tyr Phe Ile Ala
1015                    1020                    1025        1030

GCA GTG GAG AGG CTC TGG GAT TAT GGG ATG AGT AGT TCC CCA CAT GTT    3172
Ala Val Glu Arg Leu Trp Asp Tyr Gly Met Ser Ser Pro His Val
1035                    1040                    1045

CTA AGA AAC AGG GCT CAG AGT GGC AGT GGC CAG TTC CCT CAG AAG AAA GTT 3220
Leu Arg Asn Arg Ala Gln Ser Gly Ser Val Pro Gln Phe Lys Lys Val
1050                    1055                    1060

GTT TTC CAG GAA TTT ACT GAT GGC TCC TTT ACT CAG CCC TTA TAC CGT    3268
Val Phe Gln Glu Phe Thr Asp Gly Ser Phe Thr Gln Pro Leu Tyr Arg
1065                    1070                    1075

GGA GAA CTA CAT TTG GGA CTC CTG GGG CCA TAT ATA AGA GCA            3316
Gly Glu Leu His Leu Gly Leu Leu Gly Pro Tyr Ile Arg Ala
1080                    1085                    1090

GAA GTT GAA GAT AAT ATC ATG GTA ACT TTC AGA AAT CAG GCC TCT CGT    3364
Glu Val Glu Asp Asn Ile Met Val Thr Phe Arg Asn Gln Ala Ser Arg
1095                    1100                    1105        1110

CCC TAT TCC TTC TAT TCT AGC CTT ATT TCT TAT GAG GAA GAT CAG AGG    3412
Pro Tyr Ser Phe Tyr Ser Ser Leu Ile Ser Tyr Glu Glu Asp Gln Arg
1115                    1120                    1125
```

FIG. 7J

```
CAA GGA GCA GAA CCT AGA AAA AAC TTT GTC AAG CCT AAT GAA ACC AAA    3460
Gln Gly Ala Glu Pro Arg Lys Asn Phe Val Lys Pro Asn Glu Thr Lys
            1130                    1135                1140

ACT TAC TTT TGG AAA GTG CAA CAT ATG GCA CCC ACT AAA GAT GAG        3508
Thr Tyr Phe Trp Lys Val Gln His Met Ala Pro Thr Lys Asp Glu
        1145                    1150                1155

TTT GAC TGC AAA GCC TGG TAT TTC TCT GAT GTT GAC CTG GAA AAA        3556
Phe Asp Cys Lys Ala Trp Tyr Phe Ser Asp Val Asp Leu Glu Lys
    1160                    1165                1170

GAT GTG CAC TCA GGC CTG ATT GGA CCC CTT CTG TGC CAC ACT AAC        3604
Asp Val His Ser Gly Leu Ile Gly Pro Leu Leu Cys His Thr Asn
1175                    1180                    1185        1190

ACA CTG AAC CCT GCT CAT GGG AGA CAA GTG ACA GTA CAG GAA TTT GCT    3652
Thr Leu Asn Pro Ala His Gly Arg Gln Val Thr Val Gln Glu Phe Ala
            1195                    1200                1205

CTG TTT TTC ACC ATC TTT GAT GAG ACC AAA AGC TGG TAC TTC ACT GAA    3700
Leu Phe Phe Thr Ile Phe Asp Glu Thr Lys Ser Trp Tyr Phe Thr Glu
        1210                    1215                1220

AAT ATG GAA AGA AAC TGC AGG GCT GCA CCC TGC AAT ATC CAG ATG GAA GAT 3748
Asn Met Glu Arg Asn Cys Arg Ala Pro Cys Asn Ile Gln Met Glu Asp
    1225                    1230                    1235

CCC ACT TTT AAA GAG AAT TAT CGC TTC CAT GCA ATC AAT GGC TAC ATA    3796
Pro Thr Phe Lys Glu Asn Tyr Arg Phe His Ala Ile Asn Gly Tyr Ile
1240                    1245                    1250
```

FIG. 7K

```
ATG GAT ACA CTA CCT GGC TTA GTA ATG GCT CAG GAT CAA AGG ATT CGA      3844
Met Asp Thr Leu Pro Gly Leu Val Met Ala Gln Asp Gln Arg Ile Arg
1255                1260                1265                1270

TGG TAT CTG CTC AGC ATG GGC AGC AAT GAA AAC ATC CAT TCT ATT CAT      3892
Trp Tyr Leu Leu Ser Met Gly Ser Asn Glu Asn Ile His Ser Ile His
          1275                1280                1285

TTC AGT GGA CAT GTG TTC ACT GTA CGA AAA AAA GAG GAG TAT AAA ATG      3940
Phe Ser Gly His Val Phe Thr Val Arg Lys Lys Glu Glu Tyr Lys Met
     1290                1295                1300

GCA CTG TAC AAT CTC TAT CCA GGT GTT TTT GAG ACA GTG GAA ATG TTA      3988
Ala Leu Tyr Asn Leu Tyr Pro Gly Val Phe Glu Thr Val Glu Met Leu
1305                1310                1315

CCA TCC AAA GCT GGA ATT TGG CGG GTG GAA TGC CTT ATT GGC GAG CAT      4036
Pro Ser Lys Ala Gly Ile Trp Arg Val Glu Cys Leu Ile Gly Glu His
     1320                1325                1330

CTA CAT GCT GGG ATG AGC ACA CTT TTT CTG GTG TAC AGC AAT AAG TGT      4084
Leu His Ala Gly Met Ser Thr Leu Phe Leu Val Tyr Ser Asn Lys Cys
1335                1340                1345                1350

CAG ACT CCC CTG GGA ATG GCT TCT GGA CAC ATT AGA GAT TTT CAG ATT      4132
Gln Thr Pro Leu Gly Met Ala Ser Gly His Ile Arg Asp Phe Gln Ile
     1355                1360                1365

ACA GCT TCA GGA CAA TAT GGA CAG TGG GCC CCA AAG CTG GCC AGA CTT      4180
Thr Ala Ser Gly Gln Tyr Gly Gln Trp Ala Pro Lys Leu Ala Arg Leu
1370                1375                1380
```

FIG. 7L

```
CAT TAT TCC GGA TCA ATC AAT GCC TGG AGC ACC AAG GAG CCC TTT TCT    4228
His Tyr Ser Gly Ser Ile Asn Ala Trp Ser Thr Lys Glu Pro Phe Ser
1385                     1390                1395

TGG ATC AAG GTG GAT CTG TTG GCA CCA ATG ATT CAC GGC ATC AAG        4276
Trp Ile Lys Val Asp Leu Leu Ala Pro Met Ile His Gly Ile Lys
1400                     1405                1410

ACC CAG GGT GCC CGT CAG AAG TTC TCC AGC CTC TAC ATC TCT CAG TTT    4324
Thr Gln Gly Ala Arg Gln Lys Phe Ser Ser Leu Tyr Ile Ser Gln Phe
1415                     1420                1425           1430

ATC ATC ATG TAT AGT CTT GAT GGG AAG AAG TGG CAG ACT TAT CGA GGA    4372
Ile Ile Met Tyr Ser Leu Asp Gly Lys Lys Trp Gln Thr Tyr Arg Gly
1435                     1440                1445

AAT TCC ACT GGA ACC TTA ATG GTC TTC TTT GGC AAT GTG GAT TCA TCT    4420
Asn Ser Thr Gly Thr Leu Met Val Phe Phe Gly Asn Val Asp Ser Ser
1450                     1455                1460

GGG ATA AAA CAC AAT ATT TTT AAC CCT CCA ATT ATT GCT CGA TAC ATC    4468
Gly Ile Lys His Asn Ile Phe Asn Pro Pro Ile Ile Ala Arg Tyr Ile
1465                     1470                1475

CGT TTG CAC CCA ACT CAT TAT AGC ATT CGC AGC ACT CTT CGC ATG GAG    4516
Arg Leu His Pro Thr His Tyr Ser Ile Arg Ser Thr Leu Arg Met Glu
1480                     1485                1490

TTG ATG GGC TGT GAT TTA AAT AGT TGC AGC ATG CCA TTG GGA ATG GAG    4564
Leu Met Gly Cys Asp Leu Asn Ser Cys Ser Met Pro Leu Gly Met Glu
1495                     1500                1505           1510
```

FIG. 7M

```
AGT AAA GCA ATA TCA GAT GCA CAG ATT ACT GCT TCA TCC TAC TTT ACC       4612
Ser Lys Ala Ile Ser Asp Ala Gln Ile Thr Ala Ser Ser Tyr Phe Thr
        1515                    1520                    1525

AAT ATG TTT GCC ACC TGG TCT CCT TCA AAA GCT CGA CTT CAC CTC CAA       4660
Asn Met Phe Ala Thr Trp Ser Pro Ser Lys Ala Arg Leu His Leu Gln
        1530                    1535                    1540

GGG AGG AGT AAT GCC TGG AGA CCT CAG GTG AAT AAT CCA AAA GAG TGG       4708
Gly Arg Ser Asn Ala Trp Arg Pro Gln Val Asn Asn Pro Lys Glu Trp
        1545                    1550                    1555

CTG CAA GTG GAC TTC CAG AAG ACA ATG AAA GTC ACA GGA GTA ACT ACT       4756
Leu Gln Val Asp Phe Gln Lys Thr Met Lys Val Thr Gly Val Thr Thr
        1560                    1565                    1570

CAG GGA GTA AAA TCT CTG ACC AGC ATG TAT GTG AAG GAG TTC CTC           4804
Gln Gly Val Lys Ser Leu Thr Ser Met Tyr Val Lys Glu Phe Leu
        1575                    1580                    1585    1590
```

FIG. 7N

```
ATC TCC AGC AGT CAA GAT GGC CAT CAG TGG ACT CTC TTT TTT CAG AAT    4852
Ile Ser Ser Ser Gln Asp Gly His Gln Trp Thr Leu Phe Phe Gln Asn
            1595                    1600                    1605

GGC AAA GTA AAG GTT TTT CAG GGA AAT CAA GAC TCC TTC ACA CCT GTG    4900
Gly Lys Val Lys Val Phe Gln Gly Asn Gln Asp Ser Phe Thr Pro Val
            1610                    1615                    1620

GTG AAC TCT CTA GAC CCA CCG TTA CTG ACT CGC TAC CTT CGA ATT CAC    4948
Val Asn Ser Leu Asp Pro Pro Leu Leu Thr Arg Tyr Leu Arg Ile His
            1625                    1630                    1635

CCC CAG AGT TGG GTG CAC CAG ATT GCC CTG AGG ATG GAG GTT CTG GGC    4996
Pro Gln Ser Trp Val His Gln Ile Ala Leu Arg Met Glu Val Leu Gly
            1640                    1645                    1650

TGC GAG GCA CAG GAC CTC TAC TGAGGGTGGC CACTGCAG                    5035
Cys Glu Ala Gln Asp Leu Tyr
            1655            1660
```

HYBRID PROTEINS WITH MODIFIED ACTIVITY

This application is a division of application Ser. No. 08/558,107, filed Nov. 13, 1995.

The present invention relates to hybrid blood coagulation proteins with modified activities, such as enhanced coagulation activities. The hybrid proteins according to the invention can be obtained by replacing at least one region of a blood coagulation protein with at least one region from a donor anticoagulant or antithrombotic protein.

BACKGROUND OF THE INVENTION

Hybrid proteins have been described previously. For example, many hybrid proteins have been constructed to combine the functions of two proteins into one, such as an interleukin fused to a toxin. Kreitman et al., *Biochemistry* 33: 11637–44 (1994); Foss et al., Blood 84: 1765–74 (1994). In other cases, proteins have been fused to portions of other proteins that have a specific biological function. For instance, propeptides of hemostatic proteins (WO 88/03926) or stabilizing portions of albumin (WO 89/02922) have been employed in this manner.

The substitutions of various domains by domains derived from other proteins have been described for protein C (U.S. Pat. No. 5,358,932; EP 296 413), angiogenin (U.S. Pat. No. 5,286,487), fibroblast growth factor (JP-J03184998), α-interferon (EP 146 903), tissue plasminogen activator (WO 88/08451, EP 352 119) Factor V (U.S. Pat. No. 5,004,803) and Factor VIII. However, the exchange of regions between blood proteins with antagonistic functions has never been described before.

Blood proteins, which include procoagulant proteins, anticoagulant proteins and antithrombotic proteins, are among the proteins whose in vitro expression has been of great interest ever since the isolation of their corresponding genes and cDNAs. Procoagulant proteins cause coagulation to occur. In contrast, anticoagulant proteins inhibit the formation of fibrin clots, and antithrombotic proteins inhibit the formation of thrombi, which usually are larger than fibrin clots and comprise fibrin, platelets and adhesion proteins.

Blood coagulation involves a series of proteolytic events that ultimately result in the formation of an insoluble fibrin clot. The scheme of blood coagulation has been described as a cascade or "water fall," and depends on the activation properties of various serine proteases. Davie et al., *Science* 145: 1310–12 (1964); MacFarlane, *Nature* 202: 498–99 (1964). In blood, all the serine proteases involved in blood coagulation are present as inactive precursor proteins, which are activated upon proteolytic cleavage by the appropriate activator. Blood coagulation further involves non-enzymatic cofactors that control the properties of the various blood proteins. For example, Factor V and Factor VIII function as non-enzymatic cofactors for Factor Xa and Factor IXa in the intrinsic pathway of blood coagulation. See Mann et al., *Blood* 76: 1–16 (1990). Activated Factor VIIIa functions in the middle of the intrinsic coagulation cascade, acting as a cofactor for Factor X activation by Factor IXa in the presence of calcium ions and phospholipids. See Jackson, et al., *Ann. Rev. Biochem.* 49: 765 (1980).

The natural antagonist of the blood coagulation system is the anticoagulant system. In the plasma of a healthy mammalian organism, the actions of both systems are well balanced. In case of vessel injury, blood coagulation involves the deposition of a matrix of fibrin at the damaged site. After repair of the damage, the matrix of fibrin is removed by fibrinolysis.

In the anticoagulant system, a number of pathways operate to limit the extent of clot formation. Several serine protease inhibitors, such as antithrombin and heparin cofactor II, specifically interact with the activated serine proteases of the blood coagulation cascade. Additional control is provided by the protein C anticoagulant pathway, which results in the inactivation of the non-enzymatic cofactors Factor V and Factor VIII. Defects in the anticoagulant pathways are commonly associated with venous thrombosis.

Permanent and temporary disorders in blood coagulation and fibrinolysis require the administration of specific factors of the respective system. Thrombotic complications require the administration of anticoagulant proteins that are derived from the mammalian anticoagulant system, for example Protein C or Protein S.

The administration of Factor VIII, Factor IX or other blood coagulation factors is required during temporary (that is, non-genetic) blood coagulation disorders. Surgery is one type of temporary blood disorder. The various forms of hemophilia, which include genetic disorders that effect blood coagulation, also require the administration of specific coagulation factors, such as Factor VIII or Factor IX.

The functional absence of one of the procoagulant proteins involved in blood coagulation is usually associated with a bleeding tendency. The most common bleeding disorder in man is hemophilia A, an X-chromosome-linked bleeding disorder which affects about 0.01% of the male population. Hemophilia A is associated with the functional absence of Factor VIII. Hemophilia A is conventionally treated by the administration of purified Factor VIII preparations isolated from plasma of healthy donors. The treatment has several disadvantages. The supply of Factor VIII from plasma donors is limited and very expensive; the concentration of Factor VIII in blood is only about 100 ng/ml and the yields using common plasma fractionation methods are low. Additionally, although preparation methods of blood factors from human plasma have improved with regard to virus-safety, there still remains an element of risk concerning the transmission of infectious agents, including hepatitis viruses and HIV.

The isolation of a functional Factor VIII cDNA has led to the production of recombinant Factor VIII in cultured cells. Molecular cloning of Factor VIII cDNA obtained from human mRNA and the subsequent production of proteins with Factor VIII activity in mammalian, yeast and bacterial cells has been reported. See WO 85/01961; EP 160 457; EP 150 735; EP 253 455. Recombinant production has led to improvements with regard to product purity and virus safety. Factor VIII stability was not improved, however, and supply of Factor VIII from in vitro production also is limited due to low yields. Accordingly, therapy costs remain high because Factor VIII must be administered frequently.

The short in vivo half-life of wild-type Factor VIII is one reason for the frequent administration of wild-type Factor VIII in the treatment of hemophilia A. As a consequence, recipients sometimes develop antibodies against the exogenous Factor VIII that is administered, which can greatly reduce its effectiveness leading to the necessity to further increase the dose given.

For example, between 11% and 13% of the hemophilia A patients treated with Factor VIII products develop antibodies against Factor VIII. See Aledort, *Sem. Hematol.* 30: 7–9 (1993). In an attempt to induce immunotolerance, hemophilia A patients with antibodies against Factor VIII are treated with high doses of Factor VIII. Brackman et al., *Lancet* 2: 933 (1977). But high dosage administration is very expensive.

The problems-associated with factor VIII administration in the prior art may be circumvented, however, if the concentration of protein administered to obtain a Factor VIII activity in the blood of hemophiliacs can be kept sufficiently low to escape immunodetection and production of anti-Factor VIII antibodies while still obtaining the needed positive effects of Factor VIII. Accordingly, there is need for Factor VIII derivatives with improved functional properties, so that more units of Factor VIII activity can be delivered per molecule administered, thus allowing reduction in dosage and frequency of administration.

Factor VIII has three acidic regions which contain sulfated tyrosines adjacent to cleavage sites for thrombin at the regions from $Met^{337}$ to $Arg^{372}$ and from $Ser^{710}$ to $Arg^{740}$ in the heavy chain and from $Glu^{1649}$ to $Arg^{1689}$ in the light chain. See Mikkelsen et al., *Biochemistry* 30: 1533–37 (1991); Pittman et al., loc. cit. 31: 3315–25 (1992); Eaton et al., *Biochemistry* 25: 8343–47 (1986). In all three cases, the acidic regions contain one or more tyrosine residues which have been shown to be sulfated. Sulfation of $Tyr^{1680}$ is essential for the interaction of Factor VIII with von Willebrand Factor. See Leyte et al., *J. Biol. Chem.* 266: 740–46 (1991). While the role of the sulfated $Tyr^{346}$ is not known, Fay et al. *Thromb. Haemost.* 70: 63–67 (1993), such that it is likely to be involved in the interaction between the A1 and A2 domains in activated Factor VIII. Sulfation of $Tyr^{718,}$ $Tyr^{719}$ and $Tyr^{723}$ was shown to increase the intrinsic activity of activated Factor VIIIa. Michnick et al., *J. Biol. Chem.* 269: 20095–102 (1994). Functional analysis of Factor VIII-del(713-1637), a deletion mutant of Factor VIII lacking most of the B-domain and the acidic region that contains $Tyr^{718,}$ $Tyr^{719}$ and $Tyr^{723}$, showed that it was defective in procoagulant activity. Biochemical analysis revealed that full activation of Factor VIII-del(713-1637) required elevated amounts of thrombin compared to the wild-type molecule. Mertens et al., *Brit. J. Haematol.* 85: 133–42 (1993).

Thrombin is the enzyme responsible for the activation of Factor VIII. Thrombin, moreover, plays many other roles in the coagulation cascade. Proteolytic cleavage of fibrinogen by thrombin produces the fibrin monomer, which then polymerizes to form the insoluble fibrin clot. Furthermore, thrombin can initiate a number of positive and negative feedback loops that either sustain or downregulate clot formation. Stubbs et al., *Thromb. Res.* 69: 1–58 (1993); Davie et al., *Biochem.* 30: 10363–70 (1991). Binding of thrombin to its platelet receptor is associated with stimulation and aggregation of platelets (Coughlin et al., *J. Clin. Invest.* 89:351–55 (1992). Limited proteolysis by thrombin activates the non-enzymatic cofactors V and VIII, which enhances Factor X and prothrombin activation. Kane et al. *Blood* 71: 539–55 (1988). Additionally, there is evidence that thrombin is involved in the activation of Factor XI. Gailani et al., *Science* 253: 909–12 (1991). When bound to the endothelial cell receptor thrombomodulin, thrombin works as an anticoagulant by activating protein C. Esmon, *Thromb. Haemost.* 70: 29–35 (1993). In the presence of glycosaminoglycans, thrombin is specifically inhibited by the serine protease inhibitors, anti-thrombin and heparin cofactor II. Huber et al., *Biochem.* 28: 8952–66 (1989).

Determination of the three-dimensional structure of the complexes that thrombin forms with the synthetic inhibitor PPACK, as well as with hirudin, an anticoagulant protein originally isolated from leeches, have defined an important role for a positively charged area, known as the "anion exosite," in the interaction of thrombin with other proteins. Bode et al., *EMBO J.* 11: 3467–75 (1989); Skrzypczak-Jankun et al., *J. Mol. Biol.* 206: 755–57 (1989); Rydel et al., *Science* 249: 277–80 91990); Grütter et al., *EMBO J.* 9: 2361–65 (1990). The best described three-dimensional structure is that of the thrombin-hirudin complex, where the acidic region in the carboxy-terminal region of hirudin is in close contact with the anion exosite of thrombin. Grütter et al., *EMBO J* 9: 2361–65 (1990); Rydel et al., *Science* 249: 277–80 (1990). Stretches of negatively charged amino acids of the thrombin receptor, thrombomodulin and heparin cofactor II, which are similar to those in hirudin, have been shown to interact with the anion exosite of thrombin. Liu et al., *J. Biol. Chem.* 266: 16977–80 (1991); Vu et al., *Nature* 353: 674–77 (1991); Mathews et al., *Biochemistry* 33: 3266–79 (1994); Tsiang et al., *Biochemistry* 29: 10602–12 (1990); Van Deerlin et al., *J. Biol. Chem.* 266: 20223–31 (1990). Studies which employ synthetic peptides corresponding to the negatively charged areas of these proteins have shown that they have different affinities for thrombin. These studies indicate that the degree of affinity of thrombin for other proteins depends in part on the acidic regions of those other proteins. Tsiang et al., *Biochem.* 29: 10602–12 (1990); Hortin et al., *Biochem. Biophys. Res. Commun.* 169: 437–442 (1990).

In the activated state, Factor VIII is a heterotrimer comprising the amino acid residues 1–372 (containing the A1 domain) and 373–740 (containing the A2 domain) of the heavy chain and residues 1690-2332 (the domains A3-C1-C2) of the light chain. See Eaton et al., *Biochem.* 25: 505–12 (1986), and Lollar et al. *Biochemistry* 28: 666–74 (1989). In comparison with the inactive Factor VIII precursor, the active Factor VIII thus lacks the light chain fragment 1649-1689, which is involved in the interaction of Factor VIII with von Willebrand factor, Lollar et al., *J. Biol. Chem.* 263: 10451–55 (1988), as well as the complete B-domain region 741-1648.

The finding that the complete B-domain is proteolytically removed when Factor VIII is activated has led to the construction of various B-domain deletion mutants. Such Factor VIII B-domain deletion mutants were found to result in increased production levels of recombinant Factor VIII. See EP 294 910; WO 86/06101; U.S. Pat. No. 4,868,112; Toole et al., *Proc. Nat'l Acad. Sci. USA* 83: 5939–42 (1986); Eaton et al. *Biochemistry* 25: 8343–47 (1986); Sarver et al., *DNA* 6:553–64 (1987). The deletion mutant Factor VIIIdel (868-1562), which is denoted "Factor VIII dB695" here, has been shown to be similar to plasma Factor VIII with regard to binding to von Willebrand Factor, half-life and recovery of Factor VIII dB695 upon infusion into dogs with hemophilia A. Mertens et al., *Brit. J. Haematol.* 85:133–142 (1993).

Other hybrid molecules with Factor VIII activity have been described. In U.S. Pat. No. 5,004,803, for example, a Factor VIII molecule is described that retains Factor VIII activity when a Factor V B-domain is substituted for the natural B-domain. International application WO 94/11013 discloses chimeric Factor VIII in which one or more exons are substituted by the corresponding exons of Factor V and chimeric Factor V in which one or more exons are substituted by the corresponding exons of Factor VIII.

U.S. Pat. No. 5,364,771 describes human/porcine Factor VIII hybrids. These hybrids are obtained by mixing porcine Factor VIII heavy chain with human Factor VIII light chain and vice versa, or via recombinant DNA technology. A recombinant molecule with Factor VIII activity is described where the A2-domain of porcine Factor VIII has been substituted for the A2-domain of human Factor VIII. WO 94/11503 describes various constructs wherein domains of porcine Factor VIII are substituted for corresponding regions in human Factor VIII. Some of these porcine/human factor VIII hybrids exhibit increased Factor VIII activity when compared to wild-type Factor VIII, as determined by the Kabi Coatest Chromogenic Assay. The maximum increase of 3.8-fold, however, is only achieved when the large domain between amino acid positions 336 and 740 in human Factor VIII is replaced by its porcine counterpart. This domain represents the structurally but not biochemically defined unit, which is the A2-domain plus some additional amino acid residues on either side.

International applications WO 95/18827 and WO 95/18829 disclose Factor VIII derivatives wherein single amino acids in the A2 domain have been deleted or substituted to give a more stable protein with Factor VIII activity. In the latter application, only single amino acids are deleted or substituted. The procoagulant activity of all of these Factor VIII derivatives is not different from that of wild-type Factor VIII, however.

International application WO 95/18828 describes Factor VIII derivatives wherein single amino acids in the A2 domain have been deleted or substituted to give a protein with the same activity as wild-type Factor VIII, but which is reportedly capable of being prepared in greater yield by recombinant DNA techniques.

With regard to other proteins, international application WO 91/05048 discloses mutants of human plasminogen activator inhibitor whose reactive centers are replaced by the reactive center of antithrombin III. As a result, the mutants can exhibit different properties, such as reactivity with serine proteases. But this publication does not involve blood coagulation proteins, nor does it discuss the insertion of acidic regions. European application 296 413 describes a hybrid protein C whose Gla domain is replaced by another Gla domain derived from another vitamin K-dependent protein.

SUMMARY OF THE INVENTION

It therefore is an object of the present invention to provide hybrid proteins derived from blood coagulation proteins and having modified characteristics, as well as methods of making such proteins and treating patients with the hybrid proteins.

It is another object of the present invention to provide hybrid proteins that have modified characteristics by replacing at least one region in a blood coagulation protein by a region(s) from a donor protein, the donor protein being an anticoagulant or an antithrombotic protein.

It is yet another object of the present invention to provide improved hybrid proteins that have the therapeutic properties of Factor VIII.

In accomplishing these and other objects, there is provided a hybrid protein derived from a blood coagulation protein, wherein the hybrid protein comprises a region or regions from a donor anticoagulant or antithrombotic protein or from a wholly or partially synthetic polypeptide, whereby the hybrid protein has a modified biological activity.

A hybrid protein preferably is derived from a blood coagulation protein selected from the group consisting of Factor V, Factor VIII, Factor X, Factor XIII, fibrinogen, protein S and protein C. It also is preferable that the region inserted into the hybrid protein has an affinity for a serine protease, such as thrombin. This region(s) can have a greater or lesser affinity for the serine protease than native region(s) of the blood coagulation protein. Preferably, the region is an acidic region, and comprises a binding site for a serine protease. In a preferred embodiment, the region is from a protein selected from the group consisting of heparin cofactor II, antithrombin III and hirudin.

In accordance with another aspect of the present invention, there are provided hybrid proteins that comprise a first region of a blood coagulation protein and a second region of an anticoagulant or antithrombotic protein wherein (A) the second region has an affinity for a serine protease and (B) the hybrid protein has a biological activity that is characteristic of the blood coagulation protein but which is modified in the hybrid protein. The blood coagulation protein can be Factor V, Factor VIII, Factor X, Factor XIII, fibrinogen, protein S and protein C. The anticoagulant or antithrombotic protein can be antithrombin III, heparin cofactor II and hirudin. Preferably, the region from the anticoagulant or antithrombotic protein is an acidic region, and comprises a binding site for a serine protease, such as thrombin.

In accordance with still another aspect of the present invention, the blood coagulation protein is Factor VIII or a Factor VIII mutant that lacks a portion of the B-domain, such as Factor VIII db695 or Factor VIII db928. Preferably, at least one of the Factor VIII or Factor VIII mutant acidic regions located between amino acid residues 336 and 372, amino acid residues 705 and 740, preferably 712 to 737 or 718 to 732, and amino acid residues 1648 and 1689 are replaced by amino acids 53 to 62 of hirudin or amino acids 45 to 90, preferably 51 to 81, of heparin cofactor II. Additionally, the Factor VIII or Factor VIII mutant can have two or more acidic regions and/or regions having an affinity for a serine protease replaced.

In accordance with still another aspect of the present invention, there are provided pharmaceutical compositions containing hybrid proteins, polynucleotides (including vectors) encoding hybrid proteins, transformed cells containing these polynucleotides, and antibodies directed against hybrid proteins. Methods of modifying the biological activities of proteins also are provided.

These and other aspects of the present invention will become apparent to the skilled artisan in view of the disclosure contained herein. Modifications may be made to the various teachings of this invention without departing from the scope and spirit of the invention.

BRIEF DESCRIPTION OF THE FIGURES

FIGS. 7A–7N depicts the nucleotide sequence (SEQ ID NO: 1) of a Factor VIII dB695-HCII cDNA as it is contained in vector pCLB-dB695-HCII, and the amino acid sequence (SEQ ID NO: 2) encoded by the cDNA (Factor VIII dB695-HCII). The translation initiation codon is located at nucleotide position 35 and the nucleotide sequence obtained from heparin cofactor II is located from nucleotide position 2225 to nucleotide position 2315. The protein encoded by this cDNA is 1661 amino acids long.

DETAILED DESCRIPTION OF PREFERRED EMBODIMENTS

Figure 1:
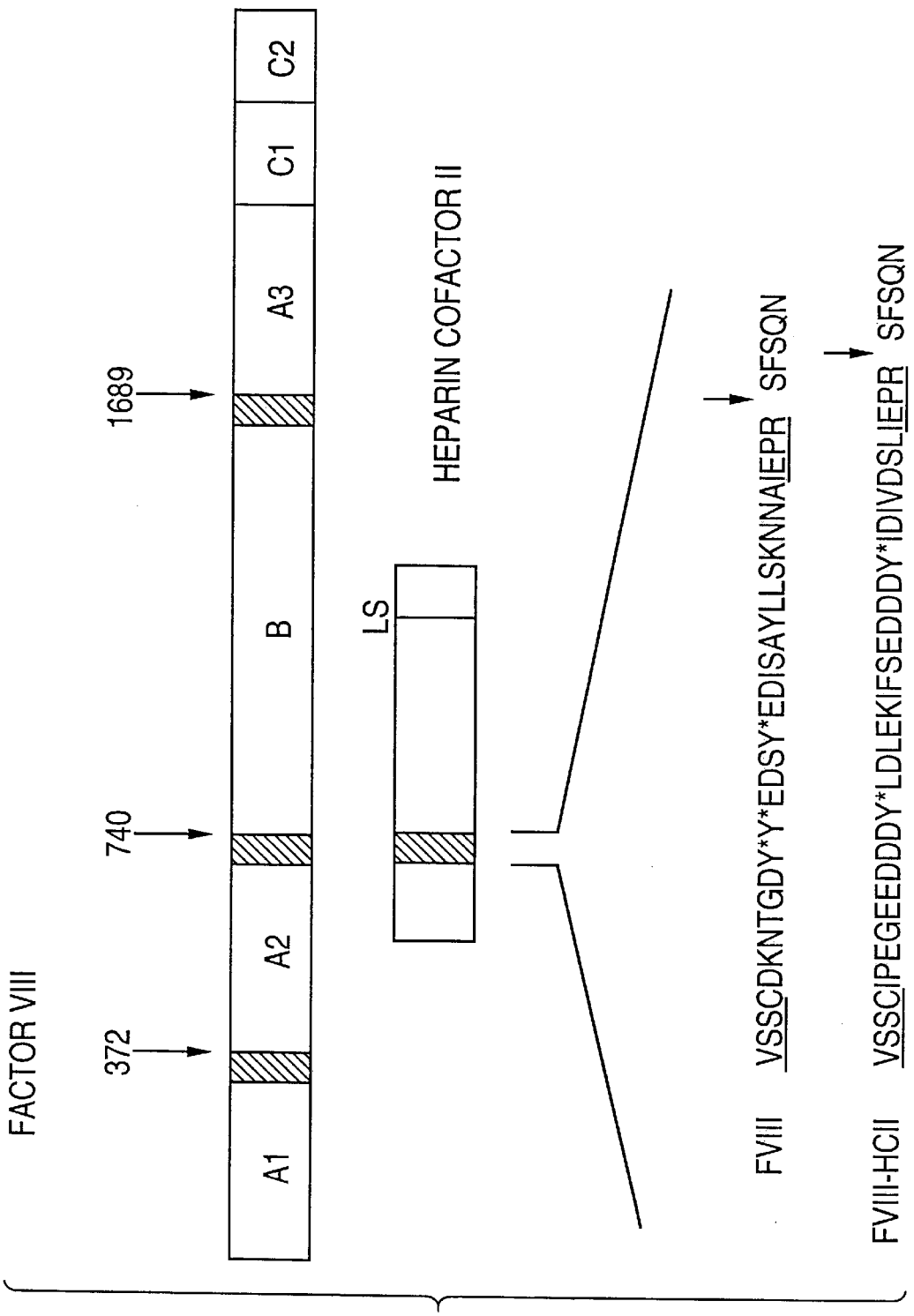
FIG. 1 is a schematic representation of Factor VIII and Heparin cofactor II. The domains of Factor VIII (A1-A2-B-A3-C1-C2) are interspersed by acidic regions at amino acid positions $Met^{373}$-$Arg^{372}$, $Ser^{710}$-$Arg^{740}$ and $Glu^{1649}$-$Arg^{1689}$ of human Factor VIII. Cleavage sites for thrombin are indicated by arrows. Similarly, an acidic region of heparin cofactor II, an inhibitor of thrombin, is located between amino acid residues 51 and 81. The reactive site of heparin cofactor II, $Leu^{444}$-$Ser^{445}$, is indicated by a vertical line (LS). In the lower section of the schematic representation, the amino acid sequences of the region from $Val^{708}$-$Ser^{746}$ of human Factor VIII and the corresponding region of Factor VIII dB695-HCII is set forth. Beneath the schematic representations, the upper amino acid sequence shows the region from $Val^{708}$-$Ser^{746}$ of human Factor VIII (FVIII), which contains an acidic region ($Ser^{710}$-$Arg^{740}$) and a cleavage site for thrombin at position $Arg^{470}$. The three sulfated tyrosines at amino acid positions 718, 719 and 723 are indicated by asterisks. The lower sequence shows the corresponding region of Factor VIII dB695-HCII FVIII-HCII). Amino acid residues derived from the A2-domain of human Factor VIII are underlined. Sulfated tyrosine residues are indicated by asterisks (SEQ ID NOS: 15 and 16).
Figure 2:
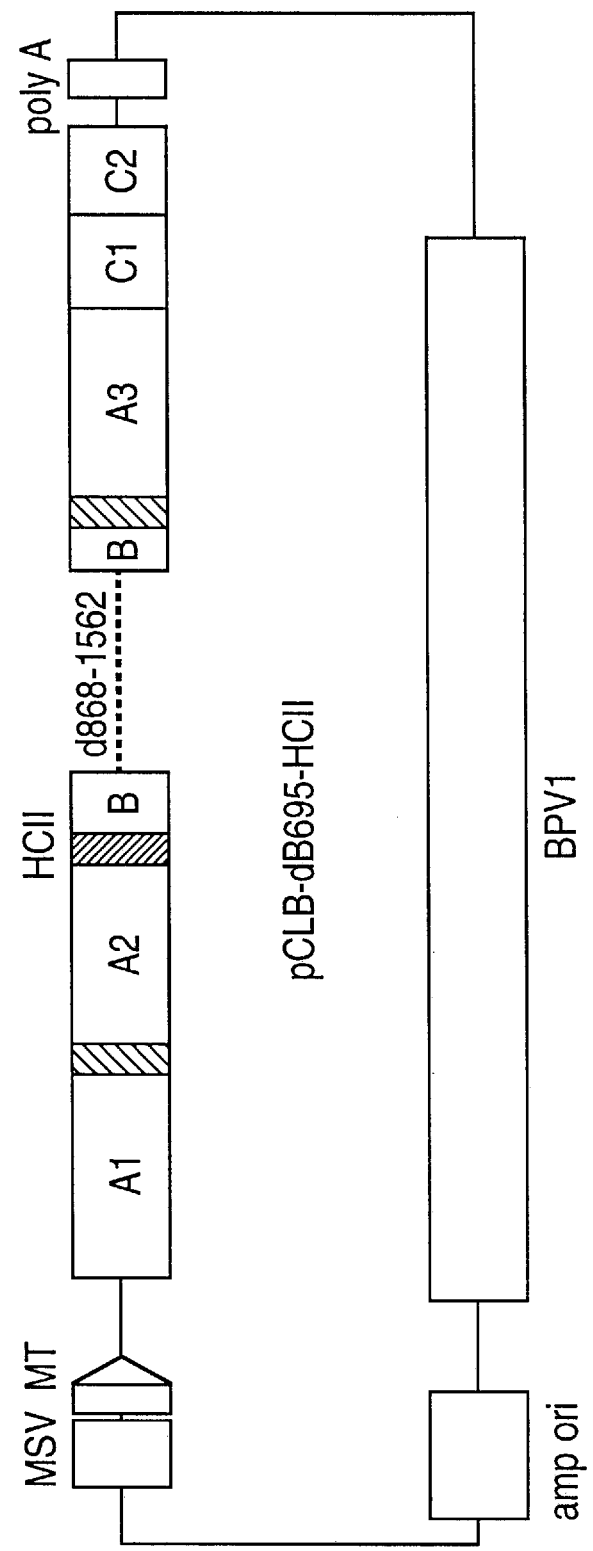
FIG. 2 is a schematic diagram of plasmid pCLB-dB695-HCII. The nucleotide sequence encoding Factor VIII dB695-HCII was inserted into plasmid pBPV (Pharmacia LKB, Sweden) and placed under the control of the metallothionein promoter (MT) and the mouse sarcoma virus (MSV) enhancer. The polyadenylation signal (poly A) is derived from SV40 and the β-lactamase gene (amp) and the origin of replication (or) are derived from the plasmid pML2, a derivative of pBR322. The presence of sequences derived from bovine papilloma virus (BPV) allows the extrachromosomal replication of the plasmid. Acidic regions derived from Factor VIII are indicated by hatched bars, the acidic region from $Ile^{51}$ to $Ser^{81}$ of human heparin cofactor II is indicated by a double-hatched bar. The deleted portion of the Factor VIII B-domain is indicated by an interrupted line.

The present invention relates to hybrid proteins that can be derived from blood coagulation proteins, which are proteins having procoagulant properties. These hybrid proteins can be created by inserting at least one region from an anticoagulant or antithrombotic protein, or synthetic polypeptides, into a blood coagulation protein. These regions preferably have an affinity for a serine protease and, more preferably, are acidic regions.

The term "derived" in its various grammatical forms connotes a similarity that is indicative of an archetype. A hybrid protein derived from a blood coagulation protein would display an activity that is characteristic of the blood coagulation protein from which the hybrid protein is derived. In particular, the characteristic activity can include the ability of a protein to interact with other proteins to cause an effect. For example, a blood coagulation protein interacts with another protein in order to ultimately cause coagulation to occur.

Surprisingly, functional hybrid proteins have been obtained by combining a region(s) from a blood coagulation protein, which is a procoagulant protein, with a region(s) from an anticoagulant and/or antithrombotic protein, which are functional antagonists of procoagulant proteins. Thus, a key aspect of the present invention is the unexpected finding that proteins that are antagonistic of one another often contain regions that are not antagonistic, but rather perform the same or similar function in the given proteins.

The hybrid proteins according to the invention can be obtained by replacing one or more regions of a blood coagulation protein with one or more regions from a donor protein, such as anticoagulant and/or antithrombotic proteins, or with synthetic polypeptides having characteristics of an appropriate region. "Replacing" in its various grammatical forms relates to changing the sequence of a protein by substituting native amino acids with different amino acids. Preferably, the replaced region of the blood coagulation protein has an affinity for a serine protease, and the region(s) from the donor protein has greater or lesser affinity for serine proteases, depending upon the properties that are desired in the resulting hybrid protein.

A protein to be altered according to the invention is a blood coagulation protein or a polypeptide derived from such a protein. In a preferred embodiment of the present invention, the hybrid protein is based upon a naturally-occurring blood coagulation protein or other source polypeptide, such as mutants of naturally-occurring proteins and polypeptide sequences modeled upon rules developed through analyses of families of proteins, as well as the characteristics of individual amino acids.

As a consequence of the inclusion of the region from the anticoagulant or antithrombotic protein, one or more biological activities of the blood coagulation protein are modified in the resulting hybrid protein. The biological activities that may be modified include activation properties, enzymatic functions, immunogenic properties. Each of these activities depend upon the primary capability of the protein to interact with other proteins, such as co-factors, enzymes, receptors or antibodies. The modification may facilitate activation of the hybrid protein as compared to the native blood coagulant protein, often by causing the hybrid protein to have an increased affinity for the appropriate activator, such as a serine protease. The alteration also may modify the enzymatic activity of the blood coagulant protein or its binding affinity for a given type of antibody.

The change in activity may be slight or significant, depending upon the nature of the region being replaced as well as the nature of the region being inserted. In fact, the modification may wholly eliminate a biological property of the hybrid protein, which is useful when protein antagonists of natural proteins are desired. An antagonistic hybrid protein would have little or no activity, but still be able to interact with the natural binding partners of the blood coagulation protein from which it is derived and thus prevent the endogenous coagulation factor from interacting with the binding partner.

The hybrid proteins according to the invention are derived from the group of procoagulant proteins. According to the present invention, the procoagulant proteins include Factor V, Factor VIII, Factor X, Factor XIII, fibrinogen, protein S and protein C or any mutant or derivative, including fragments, of any of these proteins. Plasminogen activator inhibitors and plasmin inhibitors are not procoagulant proteins, and thus are not blood coagulation proteins as defined herein.

The acidic regions employed according to the present invention preferably comprise a continuous or nearly continuous region in a protein that usually contains more than 6 and less than 100 amino acids, and includes as many acidic amino acids as to give the region an overall negative charge, that is, at least 15% of the amino acids are acidic amino acids. Preferred acidic amino acids include glutamic acid and aspartic acid.

In one embodiment, the serine protease interaction site is a thrombin binding site and the modification of the blood coagulation protein property primarily refers to the affinity of the protein for prothrombin or thrombin. The affinity of the blood coagulation protein for prothrombin or thrombin may be increased or decreased. Useful blood coagulation proteins whose affinity for thrombin may be modified according to the present invention include Factor V, Factor VIII, protein S or protein C. A modification that effects the affinity of the blood coagulation protein for prothrombin or thrombin may further effect the affinity of the blood coagulation protein for other proteins, such as other procoagulant or anticoagulant proteins or antibodies.

Acidic regions may contain tyrosine residues, which are subject to tyrosine sulfation. Each of charge, acidity and the presence of sulfate-groups in specific regions have an important influence on (i) the three-dimensional structure of the specific region and the whole protein, and (ii) the interaction of the region and/or the whole protein with other factors, like other blood proteins. Important examples of proteins with regions that contain tyrosine residues are various procoagulant and anticoagulant proteins, such as Factor V, Factor VIII, fibrinogen, heparin cofactor II, protein S, protein C or hirudin.

In one embodiment of the present invention, the acidic region of an blood coagulation protein contains one or more tyrosine residues, preferably 1 to 10 tyrosine residues, more preferably 1 to 5 tyrosine residues and most preferably 1 to 3 tyrosine residues.

According to the present invention, one or more acidic regions of an blood coagulation protein may be replaced by one or more acidic regions of one or more donor proteins. For example, an acidic region of a blood coagulation protein may further be replaced by a single acidic region or multiples thereof. Moreover, acidic regions from different proteins may replace a given acidic region or regions in an blood coagulation protein to form a hybrid protein.

According to the present invention, the donor is an anticoagulant or an antithrombotic protein. Preferably, the donor is selected from the group of heparin cofactor II, hirudin or antithrombin or any derivative, including fragments, of any of these proteins. The donor protein may further be a wholly or partially synthetic polypeptide, that is, not derived from a single natural protein, but rather modeled upon rules developed from analyses of families of proteins, as well as the characteristics of individual amino acids.

Replacement of an acidic region in a blood coagulation protein by another acidic region of a donor protein preferably occurs at the DNA level. The DNA may be obtained from genomic DNA or from a cDNA encoding the desired blood coagulation protein and donor protein regions. Replacement can be achieved with PCR and other recombinant DNA methodologies.

The DNA encoding the acidic region of the donor that should replace the acidic region in the blood coagulation protein is either amplified from a gene or from a cDNA or synthesized by a polynucleotide synthesizer. The replacement can be achieved by replacement mutagenesis or by the use of PCR-mutagenesis techniques. PCR-mutagenesis techniques do not require the amplification of the DNA encoding the acidic region from the donor, but rather can use specifically designed PCR primers, which can be synthesized by a polynucleotide synthesizer.

Site-specific and region-directed mutagenesis techniques can be employed. See CURRENT PROTOCOLS IN MOLECULAR BIOLOGY vol. 1, ch. 8 (Ausubel et al. eds., J. Wiley & Sons 1989 & Supp. 1990–93); PROTEIN ENGINEERING (Oxender & Fox eds., A. Liss, Inc. 1987). Additionally, linker-scanning and PCR-mediated techniques can be used. See PCR TECHNOLOGY (Erlich ed., Stockton Press 1989); CURRENT PROTOCOLS IN MOLECULAR BIOLOGY, vols. 1 & 2, supra. Protein sequencing, structure and modeling approaches for use with any of the above techniques are disclosed in PROTEIN ENGINEERING, loc. cit. and CURRENT PROTOCOLS IN MOLECULAR BIOLOGY, vols. 1 & 2, supra.

When the donor protein is wholly or partially a synthetic polypeptide, the DNA encoding the complete polypeptide can be synthesized by a polynucleotide synthesizer. Preferably, this DNA carries appropriate adaptors for cloning such that it can be directly used in recombinant DNA technology.

Changes in the amino acid sequence of the hybrid proteins also are contemplated in the present invention. Preferably, only conservative amino acid alterations, using amino acids that have the same or similar properties, are undertaken. Illustrative amino acid substitutions include the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; valine to isoleucine or leucine.

Additionally, variants of the hybrid proteins discussed herein can be used according to the present invention.

Variants include analogs, homologs, derivatives, muteins and mimetics of the hybrid proteins that retain the ability to cause the beneficial results described herein. The variants can be generated directly from the hybrid proteins themselves by chemical modification, by proteolytic enzyme digestion, or by combinations thereof. Additionally, genetic engineering techniques, as well as methods of synthesizing polypeptides directly from amino acid residues, can be employed.

Non-peptide compounds that mimic the binding and function of parts of the hybrid proteins ("mimetics") can be produced by the approach outlined in Saragovi et al., Science 253: 792–95 (1991). Mimetics are molecules which mimic elements of protein secondary structure. See, for example, Johnson et al.,"Peptide Turn Mimetics" in BIO-TECHNOLOGY AND PHARMACY, Pezzuto et al., Eds., (Chapman and Hall, New York, 1993). The underlying rationale behind the use of peptide mimetics is that the peptide backbone of proteins exists chiefly to orient amino acid side chains in such a way as to facilitate molecular interactions. For the purposes of the present invention, appropriate mimetics can be considered to be the equivalent of the hybrid proteins and mutants thereof.

The skilled artisan can routinely insure that such hybrid proteins according to the present invention are suitable for a given task in view of the screening techniques described herein. For example, in the circumstance where hybrid proteins derived from Factor VIII are involved, the screening techniques include tests for a cofactor and procoagulant activities.

In one particular embodiment of the present invention, the blood protein is made by using a Factor VIII molecule, or a derivative thereof, as a blood coagulation protein and human heparin cofactor II as a donor protein. Heparin cofactor II is a glycoprotein in human plasma that inhibits proteases, for example thrombin. Close to its N-terminus (from amino acid residue 51 to amino acid residue 81), heparin cofactor II carries an acidic region that contains two tyrosine sulfation sites. This region is regarded as a potential thrombin-binding site. Van Deerlin et al.,J. Biol. Chem. 266: 20223–31 (1991).

In one specific embodiment of the present invention, the region replaced in Factor VIII or a Factor VIII derivative is an acidic region. According to the desired type of modification of the biological activity of Factor VIII, one or two or all three acidic regions of Factor VIII may be replaced. The acidic regions of Factor VIII may be replaced by the acidic region of heparin cofactor II or by any other region of any one of the donor proteins mentioned above, such as heparin cofactor II, antithrombin III or hirudin. If two or more regions in the blood coagulation protein are replaced, the substituting regions may be identical or diverse, and these regions may be from the same donor protein or different donor proteins. Moreover, various types of synthetic polypeptides can be used.

Additionally, a fusion of more than one region may replace a region in an blood coagulation protein. The fused regions may be identical or different, and may be from one or more donor proteins.

It should be noted that the numbers (amino acid positions) given in this disclosure for the various regions of the blood coagulation and donor proteins make up preferred embodiments of the invention. The regions are by no means restricted to the positions given in the description of the invention. Accordingly, the regions may be larger or smaller. The regions, according to the present invention, may further be fragments of defined regions.

In one embodiment of the present invention, the region that is from human heparin cofactor II is an acidic region located between amino acid residues 51 and 81, and substitutes for any of the acidic regions of Factor VIII. The heparin cofactor II acidic region may substitute for one, two or all three acidic regions in the Factor VIII molecule. The acidic region of heparin cofactor II may further be fused to another acidic region, for example to the acidic region of hirudin, prior to replacing a region in the blood coagulation protein.

In another embodiment of the present invention, the acidic region of human heparin cofactor II, located between amino acid residues 51 and 81, substitutes for the acidic region of human Factor VIII that is located between amino acid residues 705 and 740, preferably it is the region from amino acid residue 712 to amino acid residue 737.

In another embodiment of the present invention, the hybrid human Factor VIII is derived from a human factor VIII mutant that lacks a major portion of the B-domain. For example, amino acid residues 51 and 81 of heparin cofactor II can replace an original acidic region normally found between amino acid residues 712 and 737.

Hybrid proteins also are provided that exhibit the biological activity of blood Factor VIII, yet, with increased procoagulant activity compared to cofactor activity. When administered to hemophilia patients, such hybrid proteins can correct the clotting defect by their action in the clotting cascade. Due to their increased procoagulant activity, the hybrid proteins can be administered at a lower dose and at reduced frequency compared to the proteins with Factor VIII activity described in the prior art. This is a great advantage since production as well as therapy costs can be reduced and, most importantly, the risk of raising inhibitory antibodies in hemophiliacs is decreased because more units of Factor VIII activity can be delivered per molecule.

The hybrid proteins with factor VIII activity of the present invention represent an improvement over recombinant Factor VIII molecules with regard to procoagulant activity. In one embodiment, polypeptides with Factor VIII activity disclosed in EP 294 910 are further modified according to the present invention. In this embodiment, the starting point for the construction of hybrid proteins with increased Factor VIII procoagulant activity are deletion mutants of Factor VIII in which a major portion of the B-domain has been deleted. Examples include Factor VIIIdel(868-1562), referred to herein as "Factor VIII dB695" and Factor VIIIdel (741-1668), referred to herein as "Factor VIII dB928."

Construction and sequence of Factor VIII dB695 are disclosed in EP 294 910. In one embodiment, the region from nucleotide 2191 to nucleotide 2266 of Factor VIII dB695 (encoding amino acids 712 to 737) is replaced by the region from nucleotide 208 to nucleotide 298 (encoding amino acids 51 to 80) of human heparin cofactor II. The amino acid numbers given here refer to the amino acid positions in wild-type Factor VIII; nucleotide positions refer to the numbering of wild-type Factor VIII cDNA wherein the first nucleotide of the translation initiation codon is 1. The resulting DNA construct encodes a hybrid Factor VIII referred to as "Factor VIII dB695-HCII."

The DNA construct can be placed under the control of an appropriate promoter element and inserted into an appropriate DNA expression vector. Examples of appropriate promoter elements are SV40-, CMV-, RSV-, LTR-, EBV-, b-actin-, hGH-, T4-, T3-, T7-, SP6-, metallothionein-Adeno-2, Adeno major late- or TK promoter or muscle specific promoters like the myosin promoters or inducible promoters like hsp- or β-interferon promoter or promoters from steroid hormone responsive genes. Examples of appropriate DNA expression vector systems include pBPV, pSVL, pRc/CMV, pRc/RSV, myogenic vector systems (WO 93/09236) or vectors based upon viral systems, such as poxviruses (see U.S. Pat. No. 5,445,953), adenoviruses, retroviruses or baculo viruses.

The expression vector that carries the DNA construct encoding Factor VIII dB695-HCII may be used to transform a host cell. The host cell may then be grown in a cell culture system to express the protein from the DNA. Factor VIII dB695-HCII is then isolated and purified from the progeny of the host cell or the cell culture medium used to grow the host cell. The host cell may either be a eukaryotic or a prokaryotic cell. Preferred prokaryotic hosts include E. coli and B. subtilis. Preferred eukaryotic hosts include lower eukaryotic cells, as well as mammalian cells. Preferred lower eukaryotic cells include Saccharomyces, Schizosaccharomyces, Kluyveromyces and Pichia. Preferred mammalian cells include CHO, COS, BHK, SK-HEP, C127, MRC5, 293, VERO cells, fibroblasts, keratinocytes or myoblasts, hepatocytes or stem cells, for example hematopoietic stem cells.

Factor VIII dB695-HCII is an inventive improvement of its predecessor molecule, Factor VIII dB695. Factor VIII dB695-HCII retains the desirable characteristics of Factor VIII dB695, which has already been a great improvement over the previously-existing recombinant Factor VIII molecules (EP 294 910). Factor VIII dB695-HCII has capabilities that its precursor does not have, however. The procoagulant activity of Factor VIII dB695-HCII is significantly increased compared to cofactor activity, which is a property imparted by the acidic region of heparin cofactor II.

The present invention also provides fragments and mutants of Factor VIII dB695-HCII as well as fusion proteins comprising functional portions of Factor VIII dB695-HCII, including procoagulant activity.

The present invention also provides fusion proteins, wherein Factor VIII dB695-HCII is fused to another protein or a portion of another protein. For example, Factor VIII dB695-HCII may be fused to a stabilizing portion of a serum albumin or it may be fused to a pre-pro- or pro-sequence derived from another blood factor, like Factor IX or protein S.

The invention further provides dimers and chimers of Factor VIII dB695-HCII, namely compounds having at least one biological activity of Factor VIII dB695-HCII linked to another region having substantially the same amino acid sequence as Factor VIII dB695-HCII. The individual components of a chimer may have differing amino acid sequences. Biological activity includes the ability, when administered to patients with hemophilia A, to correct the clotting defect at lower dose and with a decreased clotting time when compared to the naturally occurring Factor VIII.

To provide immunogenicity, the various Factor VIII dB695-HCII and the Factor VIII dB695-HCII molecules according to the invention may be joined covalently to a large immunogenic polypeptide entity. Such immunogenic entities are, for example, bovine serum albumin, keyhole limpet hemocyanin (KLH) and the like. These conjugated polypeptides will be used for inducing antibodies in an appropriate host organism.

According to the present invention, a full length Factor VIII cDNA, as well as any derivatives thereof, can be used as a starting material for the construction of Factor VIII/heparin cofactor II hybrids. Factor VIII cDNA, as well as any derivative thereof, may originate from any mammalian species, preferably from human, porcine or bovine sources. All forms of manipulation and application described for Factor VIII dB695-HCII apply for any Factor VIII/heparin cofactor II hybrid and are part of the instant disclosure.

In another embodiment, the present invention provides a hybrid protein, wherein the blood coagulation protein is human blood coagulation Factor VIII, or any derivative thereof, and the donor protein is hirudin. Preferably, the acidic region of hirudin, located between amino acids Phe$^{53}$ and Gln$^{62}$, replaces the acidic region of Factor VIII dB695 located between amino acid residues 705 and 740, preferably it is the acidic region from amino acid 718 to amino acid 732. The resulting hybrid protein is termed Factor VIII dB695-HIR.

Hirudin is a very potent inhibitor of thrombin and it carries a thrombin binding site with a high affinity for thrombin. Due to the replacement, Factor VIII obtains the thrombin binding site of hirudin, and acquires a high affinity for thrombin. Hirudin is the thrombin-specific anticoagulant from the leech Hirudo medicinalis. Although hirudin is not obtained from a mammalian system, it is considered to be an important antithrombotic factor.

The present invention further provides nucleic acids that encode any of the hybrid proteins according to the present invention. The nucleic acid may be DNA or RNA. The nucleic acid is contained in an expression vector that provides the appropriate elements for the expression of the DNA or RNA. The expression vector may also contain elements for the replication of said DNA or RNA. The expression vector may be a DNA or an RNA vector. Examples for DNA expression vectors are pBPV, pSVL, pRc/CMV, pRc/RSV, myogenic vector systems (WO 93/09236) or vectors based upon viral systems, for example, poxviruses (see U.S. Pat. No. 5,445,953), adenoviruses, adeno-associated virus, herpes viruses, retroviruses or baculo viruses. Examples for RNA expression vectors are vectors based upon RNA viruses like retroviruses or flaviviruses.

For gene therapy applications, the nucleic acid encoding the hybrid protein is placed within the mammal. The nucleic acids used in the genetic therapy may be chemically modified. The chemical modifications may be modifications that protect the nucleic acid from nuclease digest, for example by stabilizing the backbone or the termini. Gene therapy techniques are discussed in Culver et al., Science 256: 1550–52 (1992); Rosenberg et al., Human Gene Therapy 3: 57–75 (1992).

An expression vector containing the nucleic acid which encodes a hybrid protein according to the present invention can be used to transform host cells, which then produce the hybrid proteins. The transformed host cells can be grown in a cell culture system to in vitro produce the hybrid protein. The host cells may excrete the hybrid protein into the cell culture medium from which it can be prepared. The host cells also may keep the hybrid protein inside their cell walls and the hybrid protein may be prepared from the host cells.

The host cells may be cells obtained from mammalian cells, such as fibroblasts, keratinocytes, hematopoietic cells, hepatocytes or myoblasts, which can be transformed in vitro with an expression vector system carrying a nucleic acid according to the present invention and re-implanted into the mammal. The hybrid proteins encoded by the nucleic acid will be synthesized by these cells in vivo and they will exhibit a desired biological activity in the mammal.

In one embodiment of the invention, the mammal is a human patient suffering from hemophilia, the hybrid protein is Factor VIII dB695-HCII, which shows enhanced activation properties.

The nucleic acid encoding hybrid proteins according to the present invention, also may be used to generate transgenic animals, which express the hybrid proteins in vivo. In one embodiment, the transgenic animals may express the hybrid proteins in endogenous glands, for example in mammary glands from which the hybrid proteins are secreted. In the case of the mammary glands, the hybrid proteins can be secreted into the milk of the animals from which the hybrid proteins can be prepared. The animals may be mice, rabbits, cattle, horses, swine, goats, sheep or any other useful animal.

The expression vector containing the nucleic acid which encodes any hybrid protein according to the present invention can further be administered to a mammal without prior in vitro transformation into host cells. The practical background for this type of gene therapy is disclosed in several publications, such as WO 90/11092 and WO 94/28151. The expression vector containing the nucleic acid is mixed with an appropriate carrier, for example a physiological buffer solution and injected into an organ, preferably a skeletal muscle, the skin or the liver of a mammal. The mammal is preferably a human and more preferably a human suffering from a genetic defect, most preferably the human is suffering from a blood clotting disorder.

In one embodiment, the mammal is a human patient suffering from hemophilia and the nucleic acid that is contained in the expression vector encodes Factor VIII dB695-HCII.

The present invention provides a method for the production of antibodies that bind to hybrid proteins according to the invention. The antibodies may be monoclonal or polyclonal. Methods for the production of monoclonal or polyclonal antibodies are well known to those skilled in the art. See ANTIBODIES, A LABORATORY MANUAL, E. Harlow and D. Lane eds., CSH Laboratory (1988) and Yelton et al., *Ann. Rev. Biochem.* 50: 657–680 (1981). The antibodies can be used to determine the presence or absence of a blood protein according to the present invention or to quantify the concentration of the hybrid protein in a biological sample, for example, in a body fluid or in a cell culture medium. In one particular embodiment, said antibodies may bind to Factor VIII dB695-HCII or to Factor VIII dB695-HIR and can be used to determine the presence or absence of Factor VIII dB695-HCII or Factor VIII dB695-HIR or to quantify the concentration of Factor VIII dB695-HCII or Factor VIII dB695-HIR in a biological sample, for example in a body fluid or in a cell culture medium.

The present invention further provides a diagnostic kit that comprises antibodies that bind to hybrid proteins according to the invention. Such kits may further comprise instructions for use and other appropriate reagents, preferably a means for detecting antibodies bound to their substrate. The diagnostic kit may be used to detect the presence of a hybrid protein according to the present invention in a biological sample, such as blood, serum, plasma or urine or in a cell culture medium. It may be further used to quantify the amount of a hybrid protein according to the present invention in a biological sample, such as blood, serum, plasma or urine or in a cell culture medium.

According to the present invention, pharmaceutical compositions are provided, which include the hybrid proteins in a pharmaceutically-acceptable carrier. Pharmaceutically-acceptable carriers include aqueous solutions, non-toxic excipients, including salts, preservatives, buffers and the like, as described in REMINGTON'S PHARMACEUTICAL SCIENCES, 15th Ed. Easton: Mack Publishing Co. pp 1405–1412 and 1461–1487 (1975) and THE NATIONAL FORMULARY XIV., 14th Ed. Washington: American Pharmaceutical Association (1975), the contents of which are hereby incorporated by reference. Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobials, anti-oxidants, chelating agents and inert gases. The pH and exact concentration of the various components of the binding composition are adjusted according to routine skills in the art. See GOODMAN AND GILMAN'S THE PHARMACOLOGICAL BASIS FOR THERAPEUTICS (7th ed.). Finally, pharmaceutical compositions can include polynucleotides encoding the hybrid proteins or transformed cell comprising these polynucleotides, both of which are usually employed in the genetic therapy context.

The various pharmaceutical compositions according to the invention can be used for treating patients. These compositions include the nucleic acids encoding the hybrid proteins and the transformed mammalian cells which are capable of expressing the hybrid proteins in vivo, as well as the hybrid proteins themselves. The term "treating" in its various grammatical forms in relation to the present invention refers to preventing, curing, reversing, attenuating, alleviating, minimizing, suppressing or halting the deleterious effects of a disease state or progression or other type of abnormal state.

Patients suffering from permanent or temporary coagulation disorders can be treated with hybrid proteins derived from appropriate procoagulant proteins. For example, patients subject to hemophilia should be treated with hybrid proteins derived from Factor VIII or mutants of Factor VIII, such as Factor VIII dB695-HCII, Factor VIII dB695-HIR or any mutants thereof.

The compounds, including hybrid proteins, nucleic acids and transformed cells, as they are provided by the present invention can be used in a wide variety of in vivo and in vitro contexts. The subject compounds may be used as the active component of pharmaceutical compositions for treating patients exhibiting blood clotting deficiencies, preferably hemophilia and more preferably hemophilia A. A pharmaceutical preparation refers to any preparation to be administered to animals.

In the embodiments where the compound is a nucleic acid or a transformed cell, hybrid proteins are synthesized in vivo. All the information required for this in vivo synthesis is contained within the nucleic acid or the transformed cell. For example, a subject having undergone "genetic therapy" will have the hybrid protein appearing in the circulation, where the protein then can alleviate the symptoms associated with blood clotting deficiencies, such as hemophilia.

In preparing the pharmaceutical composition, generally the compounds are admixed with parenterally acceptable vehicles or other suitable carriers in accordance with procedures known in the art. The pharmaceutical composition, where the compound is a hybrid protein or a nucleic acid encoding such a protein, may be made into a sterile lyophilized preparation of the compound, which later may be reconstituted by addition of a sterile solution, preferably one that is isotonic with the blood of the recipient. When the compound is a transformed cell, the compound is admixed with an acceptable isotonic solution and, if necessary, further parenterally acceptable vehicles or other suitable carriers in accordance with procedures known in the art. The pharmaceutical composition may be presented in single unit or multi-dose containers, for example in sealed ampoules or vials. The ultimate use of these hybrid proteins can be based upon the use of known proteins employed to treat blood clotting deficiencies.

When the hybrid protein has a modified Factor VIII procoagulant activity, the use of the compound would be based upon that of known human Factor VIII preparations, appropriately adjusted for potency. The dose of human Factor VIII preparations as it is described in the prior art is dependent on the nature, extent and duration of the bleeding lesion as well as on the severity of the hemophilia. In general, the initial dose lies between 15 and 50 U/kg of body weight. Further administration of more or less reduced doses follow in intervals from 8 hours to several days. Hybrid proteins with modified Factor VIII procoagulant activity may deviate from the dosages needed for wild-type Factor VIII. Hybrid proteins with increased Factor VIII procoagulant activity may be employed at a reduced dose compared to wild-type Factor VIII, the initial dose lying between 1 and 100 U/kg, preferably between 1 and 50 U/kg of body weight. Additionally, the length of time between administrations may be increased. Ultimately, the reduction in dose and the increase of time between intervals of administration have to be decided individually by the attending physician.

The compound may be administered in vivo, for example by injection, intravenously, peritoneally, cutaneously, subcutaneously, or any other appropriate delivery route or mode.

Herein, data from two different test systems are used to describe Factor VIII activity. The "One Stage Clotting Assay" measures the clotting time with the effect from the addition of Factor VIII to Factor VIII deficient plasma. Principally, this test system represents an in vitro equivalent to in vivo blood clotting. Data obtained from this test depend on the ability of Factor VIII to be activated by thrombin. This ability of a Factor VIII molecule to be activated by thrombin directly affects the clotting time that is measured by the assay. The longer it takes to activate Factor VIII, the longer is the clotting time measured. In this document, Factor VIII activity is thus defined as a measurement by the One Stage Clotting Assay as "procoagulant activity."

In contrast to the One Stage Clotting Assay, the "Coatest Chromogenic Assay" measures one specific enzymatic function downstream of Factor VIII in the clotting cascade, that is, Factor Xa activity. Factor VIIIa, which is activated Factor VIII, acts as a cofactor in the activation of Factor X by Factor IXa. Since Factor Xa activity is directly dependent on Factor VIIIa cofactor activity, "Factor VIII cofactor activity" refers to the amount of Factor VIIIa in a sample.

The invention is further illustrated by the following examples, which do not limit the invention in any manner.

EXAMPLE 1

Modification of the construct pCLB-BPVdB695

A cDNA encoding Factor VIII dB695 was cloned into the plasmid pBPV (Pharmacia-LKB, Uppsala, Sweden) resulting in the plasmid pCLB-BPVdB695. Plasmid pCLB-BPVdB695 was modified as follows: a synthetic, double-stranded oligonucleotide linker (SEQ ID NO 3: sense primer: 5'-TCGACCTCCAGTTGAACATTTGTAGCA AGCCACCATGGAAATAGAGCT-3'; SEQ ID NO 4: anti-sense primer: 5'-CTATTTCCATGGTGGCTTGCTACA AATGTTCAACTGGAGG-3') containing part of the 5' untranslated region of the Factor VIII cDNA linked to a consensus-sequence for initiation of translation was fused to the restriction-site SacI at position 10 of the Factor VIII cDNA (the first nucleotide of the translation initiation codon corresponds to nucleotide 1). Introduction of this particular linker into the Factor VIII cDNA resulted in a substitution of glutamine for a glutamic acid at amino acid position-18 (the first amino acid of Factor VIII is the alanine beyond the signal sequence cleavage site). The 3' end of the Factor VIII dB695 cDNA was modified by using a synthetic double stranded linker (sense primer SEQ ID NO 5: 5'-GGGTCGACCTGCAGGCATGCCTCGAGCCGC-3'; anti-sense primer SEQ ID NO 6: 5'-GGCCGCGGCTC GAGGCATGCCTGCAG GTCGACCCTGCA-3'), which was inserted into the PstI-site at nucleotide position 7066 of Factor VIII. This modification resulted in an abridged 3' non-coding region of the Factor VIII cDNA. Both the modified 5' and 3' ends were cloned into the plasmid pBPV, which had been digested with XhoI and NotI. The resulting plasmid was termed pCLB-dB695 and served as starting material for the construction of modified Factor VIII proteins.

According to the present invention, the modified plasmid pCLB-dB695 can be used as a template for the construction of Factor VIII hybrids which contain amino acid sequences from a donor protein. DNA sequences encoding the amino acid sequences from a donor protein are inserted into the Factor VIII dB695 coding region of pCLB-dB695, either in addition to the sequence encoding Factor VIII dB695 or substituting for a portion thereof. Insertion of these sequences leads to Factor VIII hybrid proteins with modified activity, such as increased procoagulant activity.

EXAMPLE 2

Isolation of a part of human heparin cofactor II from liver cDNA

For the isolation of a part of heparin cofactor II cDNA from liver cDNA, PCR technology was employed. The oligonucleotide primers used in the PCR contained portions of the Factor VIII cDNA.

The primers used for amplification of the cDNA fragment encoding the region from $Ile^{51}$ to $Ser^{81}$ of heparin cofactor II from total liver cDNA were: sense primer SEQ ID NO 7: 5'-C T G A A G G T T T C T A G T T G T / ATTCCAGAGGGGAGGAG-3' (position 2173-2191 in Factor VIII cDNA/position 208-226 in heparin cofactor II cDNA) and antisense primer SEQ ID NO 8: 5'-G G A G A A G C T T C T T G G T T C A A T / CAGACTGTCGACGATGTC-3' (position 2266-2287 in Factor VIII cDNA/position 280-298 in heparin cofactor II cDNA. The slash ("/") represents the border between Factor VIII and heparin cofactor II originated sequences).

The first nucleotides of Factor VIII cDNA and heparin cofactor II cDNA correspond to the first nucleotide of the translation initiation codon of the two proteins, respectively. According to the numbering system employed herein, position 2173-2191 corresponds to a sequence that includes nucleotides 2173 up to 2190, but does not include nucleotide 2191. The same system of numbering is employed for the amino acids. This numbering system is employed throughout this application.

The polymerase chain reaction (PCR) was used to amplify a 129 bp fragment that contained a fusion of amino acid sequence $Leu^{706}$-$Asp^{712}$ (up to but not including $Asp^{712}$) of Factor VIII, amino acid sequence $Ile^{51}$-$Ser^{81}$ (up to but not including $Ser^{81}$) of heparin cofactor II and amino acid sequence $Ile^{737}$-$Gln^{744}$ (up to but not including $Gln^{744}$) of Factor VIII. Reaction conditions were: 2' 90° C., 20'50° C., 3' 72° C.; 37 times 45" 90° C., 90" 50° C., 3' 72° C.; 5' 65° C. ('=minutes, "=seconds) in the presence of 1 mM dNTPs, Pfu-polymerase reaction buffer, 50 pMol of the sense primer SEQ ID NO 7, 50 pM of the antisense primer SEQ ID NO 8 and 2.5 U of Pfu-polymerase (Stratagene, Cambridge, UK). Human liver cDNA was prepared as described previously (Leyte et al., *J. Biochem.* 263: 187–94 (1989) and used as a template. The PCR-product was a 129 bp fragment representing an in frame fusion of a portion of Factor VIII and a portion of heparin cofactor II.

EXAMPLE 3
Fusion of Factor VIII heparin cofactor II sequence with pCLB-dB695

In the previous example, the isolation of a fragment of the heparin cofactor II cDNA is described using oligonucleotide primers that are at least partially based upon the Factor VIII cDNA. Employing these specific primers, the portion of the heparin cofactor II cDNA that has been isolated can be introduced at a specific site in the Factor VIII cDNA. Using modifications of the methods described in this example, other cDNA sequences may be fused with the Factor VIII cDNA. Additionally, fusions at sites different from that indicated in this particular example may be used.

The PCR primers employed to insert the Factor VIII/heparin cofactor II fusion site into pCLB-dB695 were the sense primer SEQ ID NO 9: 5'-TCTAGCTTCAGGACTCATTGG-3' (nucleotide 1683–1704 of Factor VIII) and the antisense primer SEQ ID NO 10: 5'-ATACAACTAGAAACCTTCAG-3' (nucleotide 2173-2191 of Factor VIII and nucleotide 208-210 of heparin cofactor II).

The polymerase chain reaction was used to amplify a 510 bp fragment that contained nucleotide 1683-2191 of Factor VIII and nucleotide 208-210 of heparin cofactor II. Reaction conditions were: 2' 90° C., 20' 50° C., 3' 72° C.; 37 times 45" 90° C., 90" 50° C., 3' 72° C.; 5' 65° C. in the presence of 1 mM dNTPs, Pfu-polymerase reaction buffer, 50 pMol of sense primer (1683-1704) SEQ ID NO 9 and 50 pMol of antisense primer (2173-2191) SEQ ID NO 10 and 2.5 U of Pfu-polymerase (Stratagene, Cambridge, UK). Both the 510 bp fragment, as well as the 129 bp fragment described in Example 2, were purified by low-melting agarose followed by phenol extraction and ethanol precipitation. Subsequently, 1 ng of both fragments were used as a template for the polymerase chain reaction employing the above PCR primers SEQ ID NO 9 and SEQ ID NO 8. Reaction conditions were: 2' 90° C., 20' 50° C., 3' 72° C.; 37 times 45" 90° C., 90" 50° C., 3' 72° C.; 5' 65° C. in the presence of 1 mM dNTPs, Pfu-polymerase reaction buffer, 50 pMol of primer SEQ ID NO 9 and SEQ ID NO 8 and 2.5 U of Pfu-polymerase (Stratagene, Cambridge, UK). The resulting fragment of 619 bp was digested with BamHI and HindIII, resulting in a 423 bp fragment in which the region of Factor VIII from nucleotide 2191 to 2266 of Factor VIII was replaced by the region from nucleotide 208 to 298 of heparin cofactor II. The 423 bp BamHI-HindIII fragment which contained the hybrid Factor VIII-heparin cofactor II-sequence was used to replace the corresponding fragment of pCLB-dB695. Following transformation into *E. coli* DH1, clones containing the Factor VIII dB695-heparin cofactor II fusion cDNA were selected based upon restriction digestion analysis. The resulting plasmid was termed pCLB-dB695-HCII and the sequence of the 423 bp fragment that contained the sequence obtained from heparin cofactor II was verified by oligonucleotide sequencing. The complete sequence of the Factor VIII dB695-HCII cDNA and the amino acid sequence it codes for are depicted in FIGS. 7A–7N.

EXAMPLE 4
Expression of pCLB-dB695 and pCLB-dB695-HCII in C127 cells

In Example 3, the construction of a cDNA encoding a hybrid protein having amino acid sequences obtained from Factor VIII and heparin cofactor II is outlined. The resulting cDNA was cloned into plasmid pBPV, which is commonly used for expression of proteins in eukaryotic cells. Here, the methods for expression of proteins encoded by pCLB-dB695-HCII and pCLB-dB695 in C127 cells are discussed. Similarly, other eukaryotic and prokaryotic cells may be used for the expression of different cDNAs encoding hybrid Factor VIII proteins.

C127 cells were maintained in Iscove's medium supplemented with 10% fetal calf serum, 100 U/ml penicillin and 100 mg/ml streptomycin. Subconfluent monolayers of C127 cells were transfected by the $CaPO_4$-method, essentially as described in Graham et al. *Virology* 52: 456–67 (1973). Both plasmids, pCLB-dB695-HCII (20 μg) as well as pCLB-dB695 (20 μg) were cotransfected with pPGKhyg (1 μg; Ten Riele et al., *Nature* 348: 649–51 (1990). Following transfection and selection of transfected cells with 200 μg/ml of hygromycin, individual clones were isolated and propagated in selective medium. The secretion of Factor VIII was monitored by measuring the ability of Factor VIII to function as a cofactor for the Factor IXa-dependent conversion of Factor Xa, employing a chromogenic substrate for Factor Xa (Coatest Factor VIII, Chromogenix, Mölndal, Sweden).

Factor VIII antigen was determined using monoclonal antibodies that have been characterized previously (Lenting et al., *J. Biol. Chem.* 269: 7150–55 (1994). Monoclonal antibody CLB-Cag 12, directed against the Factor VIII-light chain was used as a solid phase, while peroxidase-labelled monoclonal antibody CLB-Cag117, also directed against the Factor VIII light-chain, was used to quantify the amount of immobilized Factor VIII. As a standard, normal plasma obtained from a pool of 40 healthy donors was used. Procoagulant activity was determined in a one-stage clotting assay, using congenitally Factor VIII-deficient plasma. Prior to analysis, conditioned medium was mixed with 1/5 volume of a 3.8% sodium citrate solution and diluted at least 5-fold before testing in the coagulation assay. Clones of cells that produced significant amounts of Factor VIII dB695 or Factor VIII dB695 HCII, respectively, were selected for further analysis. The proteins that were expressed by the selected cell clones were analyzed by the methods described above.

Mertens et al., *Brit. J. Haematol.* 85: 133–42 (1993), have described the properties of Factor VIII del(868-1562), referred to here as "Factor VIII dB695." One clone obtained from cells transfected with pCLB-dB695 (clone 14-6521) and one obtained from cells transfected with pCLB-dB695-HCII (clone 14-6310) were grown to confluency and, subsequently, cofactor activity, procoagulant activity and Factor VIII antigen levels were determined in the manner discussed above, and the data are presented in Table I.

TABLE I

| Factor VIII protein | cofactor activity | procoagulant activity | Factor VIII antigen | ratio procoagulant/ cofactor activity |
|---|---|---|---|---|
| Factor VIII dB695 | 174 ± 10 | 164 ± 32 | 177 ± 33 | 0.94 ± 0.19 |
| Factor VIII dB695-HCII | 157 ± 13 | 267 ± 20 | 174 ± 32 | 1.70 ± 0.18 |

Factor VIII procoagulant activity refers to the activity as measured by a one-stage clotting assay, which relates to the ability of Factor VIII to be activated, whereas Factor VIII cofactor activity refers to the spectrometric assay, which monitors the formation of Factor Xa. Antigen levels were measured with an ELISA that was specific for the Factor VIII light chain. Values are the mean (±standard deviation) of five different samples for each mutant. Factor VIII procoagulant activity, chromogenic activity and antigen are given in mU/ml conditioned medium. The data obtained show that conditioned medium obtained from clone 14-6521 (Factor VIII dB695) and clone 14-6310 (Factor VIII dB695-HCII) displayed similar cofactor activity. Furthermore, Factor VIII antigen levels were similar for Factor VIII dB695 and Factor VIII dB695-HCII. Investigation of the procoagulant properties of both Factor VIII mutants revealed a procoagulant activity for Factor VIII dB695 that was roughly equivalent to its cofactor activity and antigen levels. Surprisingly, the pro-coagulant activity of Factor VIII dB695-HCII was 1.7 times higher then the activity found in the cofactor activity assay and antigen levels. The increased procoagulant activity of Factor VIII dB695-HCII can be explained by a lower activation threshold, which would not have been expected in view of the scientific literature. Factor VIII dB695-HCII is activated at a lower thrombin level than other known molecules with Factor VIII activity.

This ability to be activated with lower levels of thrombin is demonstrated in Table III (see below). Factor VIII dB695-HCII is activated approximately eight times faster than Factor VIII dB695. Consequently, at a site of vascular injury, any amount of thrombin generated results in the increased activation of Factor VIII dB695-HCII, enabling this molecule to act as a procoagulant compound with an increased efficiency compared to other compounds with Factor VIII activity. In other words, Factor VIII dB695-HCII is activated at a much earlier timepoint in the events of blood coagulation. As a consequence, Factor VIII dB695-HCII can be administered to hemophilia A patients at a much lower dose and at a reduced frequency than other molecules with Factor VIII activity. This highly reduces the risk of inhibitory antibody production in the patients. This further reduces production and medication costs.

EXAMPLE 5
Detection of the Factor VIII dB695-HCII cDNA in stably transfected C127 cells In the previous examples, the construction, expression and characterization of the hybrid protein Factor VIII dB695-HCII have been described. To verify the sequence of the Factor VIII dB695-HCII hybrid protein in C127 cells stably transfected with pCLB-dB695-HCII (clone 14-6310), DNA was isolated from this particular cell line and a fragment of the inserted Factor VIII cDNA that contained the heparin cofactor II-sequence was PCR amplified with help of the PCR using the following oligonucleotide primers: sense primer SEQ ID NO 11: 5'-GTAGATCAAAGAGGAAACCAG-3' (nucleotide 1732-1753 of Factor VIII) and antisense primer SEQ ID NO 12: 5'-GTCCCCACTGTGATGGAGC-3' (nucleotide 2577-2596 of Factor VIII). PCR conditions were: 2' 90° C., 5' 50° C., 3' 72° C.; 37 times 45" 90° C., 90" 50° C., 3' 72° C.; 5' 65° C. in the presence of 1 mM dNTPs, Taq-polymerase reaction buffer, 50 pMoles of sense primer, 50 pMoles of antisense primer, and 2.5 U of Taq-polymerase. The resulting 879 bp fragment was cloned into the PGEM-T vector (Promega, Madison, Wis.) and the sequence of the insert was determined employing Taq DNA polymerase (Promega, Madison, Wis.). Inspection of the nucleotide sequence of the amplified fragment revealed that the Factor VIII-heparin cofactor II fusion site was present in the cell line. No nucleotide substitutions compared to the nucleotide sequence of the Factor VIII dB695-HCII DNA as depicted in FIGS. 7A–7N were detected.

EXAMPLE 6
Characterization and processing of purified Factor VIII dB695-HCII and Factor VIII dB695

As shown in example 4, the hybrid protein Factor VIII dB695-HCII present in the conditioned medium of cells transfected with pCLB-dB695-HCII displays an increased procoagulant activity compared to Factor VIII dB695. Further characterization of Factor VIII dB695-HCII was performed following purification from conditioned medium of transfected cells. Purification was performed by immunoaffinity chromatography essentially as described in Mertens et al., *Brit. J. Haematol.* 85: 133–42 (1993). First, the procoagulant and cofactor activities of the purified Factor VIII dB695-HCII was assessed and compared to purified Factor VIII dB695. The results are shown below in Table II.

TABLE II

| Factor VIII | procoagulant activity (U/ml; n = 3) | cofactor activity (U/ml; n = 4) |
|---|---|---|
| Factor VIII dB695-HCII | 185 ± 14 | 105 ± 35 |
| Factor VIII dB695 | 95 ± 38 | 96 ± 25 |

Cofactor activity and procoagulant activity were determined as described previously. Mertens et al., *Brit. J. Haematol.* 85: 133–142 (1993). Values are given as the mean (±standard deviation) of different samples (n=number of different samples). The data in table II show that the ratio of procoagulant activity over cofactor activity is 1.8 for Factor VIII dB695-HCII and 1.0 for Factor VIII dB695. In agreement with the data obtained in the conditioned media of the transfected cells purified Factor VIII dB695-HCII displays an increased procoagulant activity.

Next, the subunit composition of Factor VIII dB695-HCII and compared it to the subunit composition of purified Factor VIII dB695 was determined. Gel electrophoresis with a 7.5% SDS-PAGE, followed by immunoblotting with monoclonal and polyclonal antibodies directed against various domains of Factor VIII, was performed for both proteins. Antibodies: CLB-CAg 69; MAS530; pA2 (an affinity-purified polyclonal antibody directed against a peptide that corresponds to amino acid sequence $Ile^{480}$-$Leu^{498}$ of Factor VIII) and CLB-CAg 9 were employed. The data indicated that Factor VIII dB695-HCII is processed properly into a light and a heavy chain and its subunit composition is the same as that of Factor VIII dB695.

Monoclonal antibody CLB-CAg69, directed against the amino-acid sequence $Lys^{1673}$-$Arg^{1689}$ at the amino-terminus of the Factor VIII light chain, revealed the presence of two bands that correspond to the Factor VIII light chain and single chain unprocessed Factor VIII, respectively.

Monoclonal antibody MAS530 (Sera-Lab, Sussex, England) directed against the heavy chain of Factor VIII, recognizes single chain Factor VIII dB695-HCII and in addition reacts with several other bands which represent the Factor VIII heavy chain with variable portions of the Factor VIII B-domain attached. Immunoblot analysis of purified Factor VIII dB695 with the same monoclonal antibodies yields identical results.

An affinity-purified polyclonal antibody directed against a synthetic peptide that corresponds to $Ile^{480}$-$Leu^{498}$ of Factor VIII was found to react in a similar manner as monoclonal antibody MAS530. Monoclonal antibody CLB-CAg 9 is directed against the peptide Asp$^{721}$-Asn735, a sequence that is not present in Factor VIII dB695-HCII. As expected, Factor VIII dB695-HCII does not react with this particular antibody. In contrast, purified Factor VIII dB695 readily reacts with monoclonal antibody CLB-CAg 9 and the pattern obtained is identical to that obtained for monoclonal antibody MAS530 which is also directed against the Factor VIII heavy chain.

These results show that proteolytic processing and subunit composition of Factor VIII dB695-HCII is identical to Factor VIII dB695. The difference between Factor VIII dB695 and Factor VIII dB695-HCII, however, is the surprisingly increased procoagulant activity of the hybrid protein. Therefore, these data indicate that Factor VIII dB695-HCII can be used as an improved reagent for the treatment of the congenital bleeding disorder hemophilia A.

EXAMPLE 7

Thrombin activation of Factor VIII dB695-HCII and Factor VIII dB695

Figure 5:
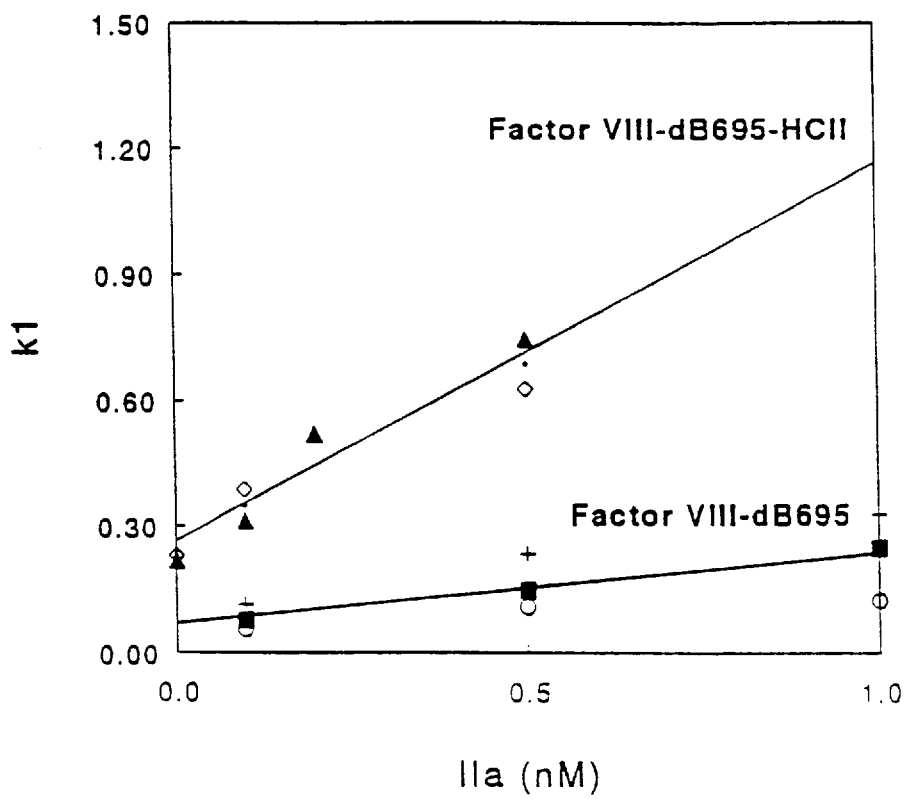
FIG. 5 depicts the rate constants of thrombin activation of Factor VIII dB695 and Factor VIII dB695-HCII. Factor VIII activation was monitored at different concentrations of thrombin, as shown in FIGS. 3 and 4. For every thrombin concentration used, the first order rate constant of Factor VIII activation ($k_1$) was determined. From the slope of a plot of the first order rate constant $k_1$ against the concentration of thrombin, the second order rate constants of activation of Factor VIII dB695 and Factor VIII dB695-HCII were determined (see Table III). Data points correspond to Factor VIII dB695 (■, ○, +) and Factor VIII dB695-HCII (▲, ◊). For Factor VIII dB695, the results of three different experiments are given. For Factor VIII dB695-HCII the results of two different experiment are displayed. At the x-axis the concentration of thrombin is depicted (1 nM); at the y-axis the first order rate constant of activation (k1) that is derived from equation 3 is given (M $min^{-2}$).

Examples 4 and 6 show that Factor VIII dB695-HCII displays an increased procoagulant activity compared to Factor VIII dB695. Determination of the second-order rate constant of cleavage by thrombin for both Factor VIII dB695-HCII and Factor VIII dB695, as it is depicted in FIG. 5, has further shown that less thrombin is required to activate Factor VIII dB695-HCII compared to Factor VIII dB695.

Activation of Factor VIII was determined employing the following reagents. Phospholipid vesicles were prepared from equimolar concentrations of L-a-phosphatidylcholine (egg yolk) and L-a-phosphatidylserine (human brain) (Sigma, St. Louis, U.S.A.). Factor IXa, thrombin, Factor X and Factor Xa were prepared as described previously and the concentration of the different protein preparations was determined by active-site titration (Mertens et al., *J. Biochem.* 223: 599–605 (1984)). Proteins used in this study were homogeneous as judged by SDS-polyacrylamide gel electrophoresis. Factor X was acetylated using procedures described previously (Neuenschwander et al., *Analyt. Biochem.* 184: 347–52 (1990)).

Activation of Factor VIII dB695 and Factor VIII dB695-HCII by thrombin was monitored as follows: Phospholipid vesicles (final concentration 100 mM) were allowed to aggregate for 10 min at 37° C. in a Ca$^{2+}$-containing buffer (50 mM Tris HCl pH=7.5, 150 mM NaCl and 10 mM CaCl$_2$). Subsequently, 0.1 nM of Factor IXa, 0.2 mM acetylated Factor Xa and 0.5 U/ml Factor VIII were added. Activation of Factor VIII was initiated by the addition of various concentrations of thrombin. The amount of Factor Xa formed in time in the reaction mixture was assessed by sub-sampling 50 ml of the reaction mixture into stop buffer containing 50 mM Tris-HCl pH=7.5, 150 mM NaCl, 5 mM EDTA, 50 U/ml hirudin, 100 mg/ml egg ovalbumin and the synthetic substrate Pefachrome Xa (Pentapharm AG, Basel, Switzerland).

Figure 3:
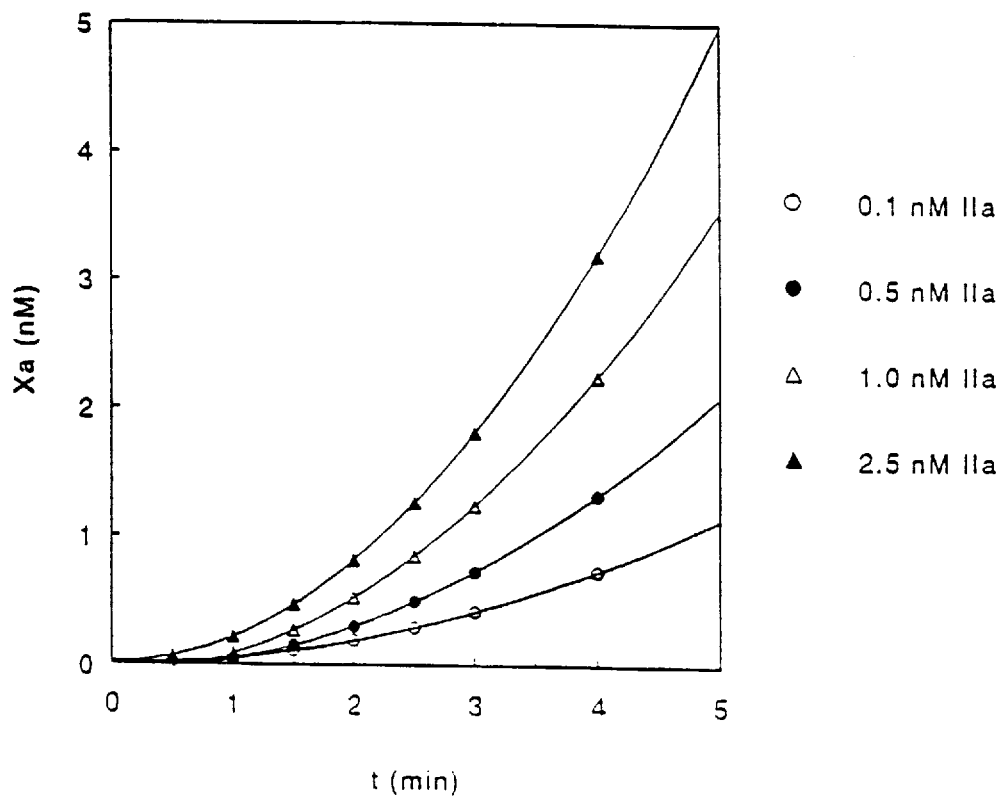
FIG. 3 depicts the activation of Factor VIII dB695 by thrombin. Activation of acetylated Factor X was performed in the presence of 0.1 nM Factor IXa, 100 mM phospholipids and 0.2 nM Factor VIII in 100 mM NaCl, 10 mM $CaCl_2$, 50 mM Tris (pH 7.5) at 37° C. The reaction was initiated by the addition of different concentrations of thrombin: 0.1 nM (○), 0.5 nM (●), 1.0 nM (Δ) and 2.5 nM (▲). The amount of Factor Xa generated in time was monitored by subsampling into 50 μl of stop buffer and the addition of the chromogenic substrate Pefachrome Xa.
Figure 4:
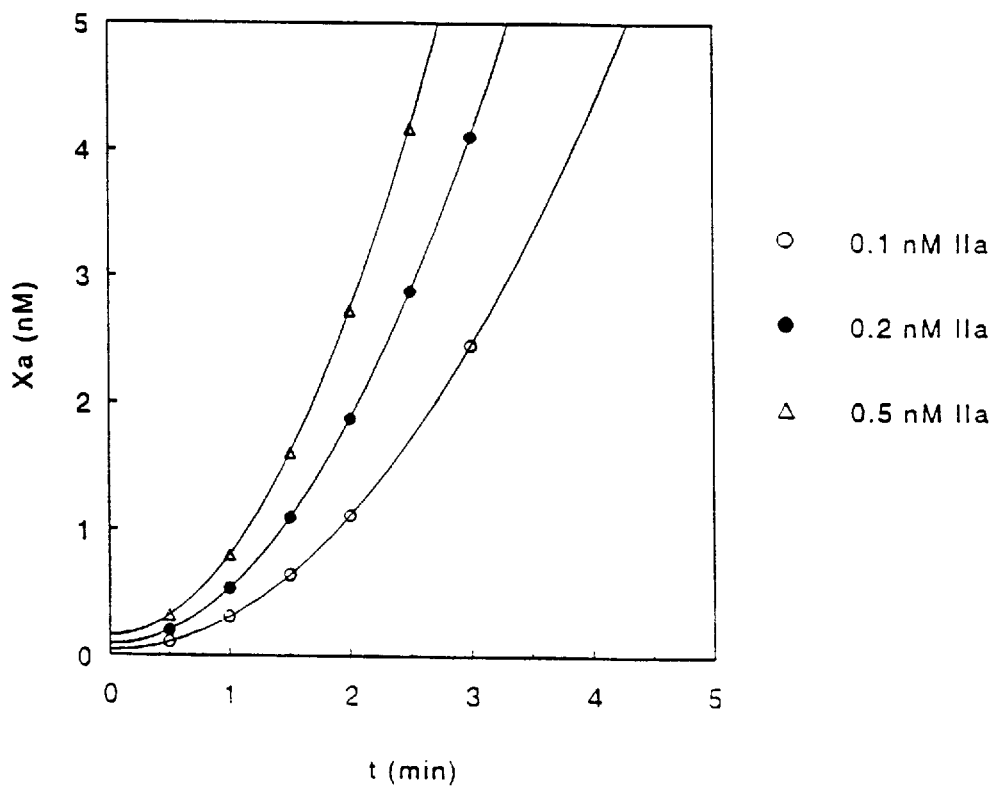
FIG. 4 depicts the activation of Factor VIII dB695-HCII by different concentrations of thrombin: 0.1 nM (○); 0.2 nM (●) and 0.5 nM (Δ). The experiment was performed under the conditions as in FIG. 3.

Conversion of the substrate Pefachrome Xa was monitored at 405 nm and active-site titrated Factor Xa was used as a standard. In FIG. 3, activation of Factor VIII dB695 is depicted for several concentrations of thrombin. The amount of Factor Xa generated is related to the concentration of thrombin used for activation. Using the following set of reactions, an equation that describes the activation of Factor VIII adequately can be obtained:

Step 1:
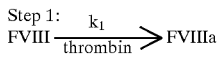

Step 2:
FVIIIa – FIXa +

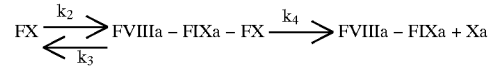

where $K_1$–$K_4$ constitute the rate constants of the different reaction steps. In Step 1 of this reaction strategy, the activation of Factor VIII by thrombin is depicted. The Factor VIIIa-Factor IXa complex efficiently catalyzes the phospholipid-dependent conversion of Factor X into Factor Xa.

In the experiments performed, phospholipids were used in high concentrations. As a consequence the interaction of the different components with phospholipids is not considered to be rate-limiting. The conversion of Factor X into its activated form (Step 2) is analyzed according to standard Michaelis-Menton kinetics, resulting in the following equation:

$$\frac{d[FXa]}{dt} = \frac{K_4[FVIIIa - FIXa - FX]_t[FX]_t}{Km + [FX]_t} \quad (1)$$

where $K_m=(k_3+k_4)/k_2$ and $[FX]_t=[FX]_0$. The concentration of Factor VIIIa increases in time from $[FVIIIa]_0$ (=0) to $[FVIIIa]_t$. By using appropriate concentrations of activator during the initial phase of Factor Xa formation, Factor VIII activation can be analyzed according to the method of initial rates of activation.

$$[FVIIIA]_t = k_1[FVIII]_0^t \quad (2)$$

Combining equation (1) and (2) and subsequent integration between t=0 and t=t results in the following expression of Factor Xa formation in time:

$$[FXa]_t = \frac{k_4 k_1 [FVIII]_0 [FX]_0}{Km + [FX]_0} t^2 + [FXa]_0 \quad (3)$$

Equation 3 is very similar to the usual solution for a complex kinetic system comprising two coupled enzymatic reaction steps. (Chibber et al., *Biochemistry* 24: 3429–34 (1985). The values of a number of parameters in Equation 3 are known. The Factor X activation rate constant k4 in the presence of Factor VIII dB695 and Factor VIII dB695 are 11.5±5.2 min$^{31}$ and 17.2 ±5.5 min$^{-1}$, respectively which have been determined experimentally from the rate of Factor Xa formation at steady state conditions. The Michaelis constant (Km) is 200 nM for human coagulation factors Factor VIIIa and Factor IXa (Jesty, *Haemostasis* 21: 208–18 (1991) and $[FVIII]_0=0.2$ nM and $[FX]_0=0.2$ mM. The data obtained were fitted into Equation 3 using Enzfitter software (Elsevier, The Netherlands). For each thrombin concentration used to activate Factor VIII dB695, a first order constant can be obtained that is dependent on the thrombin concentration employed. The slope of a plot of the thrombin-concentration used for activation of Factor VIII dB695 against the first-order constant ($k_1$) yields a second-order constant of activation (FIG. 5). In table III, the values of the second-order constant of activation are given for both Factor VIII dB695 and Factor VIII dB695-HCII. The values of the second order constant of activation reveal that Factor VIII dB695-HCII is activated by thrombin eight times as fast as Factor VIII dB695.

TABLE III

| Factor VIII protein | second order rate constant $(M^{-1} s^{-1} \times 10^{-6})$ |
|---|---|
| Factor VIII obtained from plasma | 2.1 ± 0.2 |
| Factor VIII dB695 | 3.0 ± 0.8 |
| Factor VIII dB695-HCII | 23.2 ± 0.5 |

The second-order rate constant of activation of both Factor VIII dB695 and Factor VIII dB695-HCII by thrombin was determined from the slope of FIG. 5. Values are given in $M^{-1}s^{-1}$±S.E.

EXAMPLE 8
Construction of a Factor VIII-hirudin hybrid protein

Figure 6:
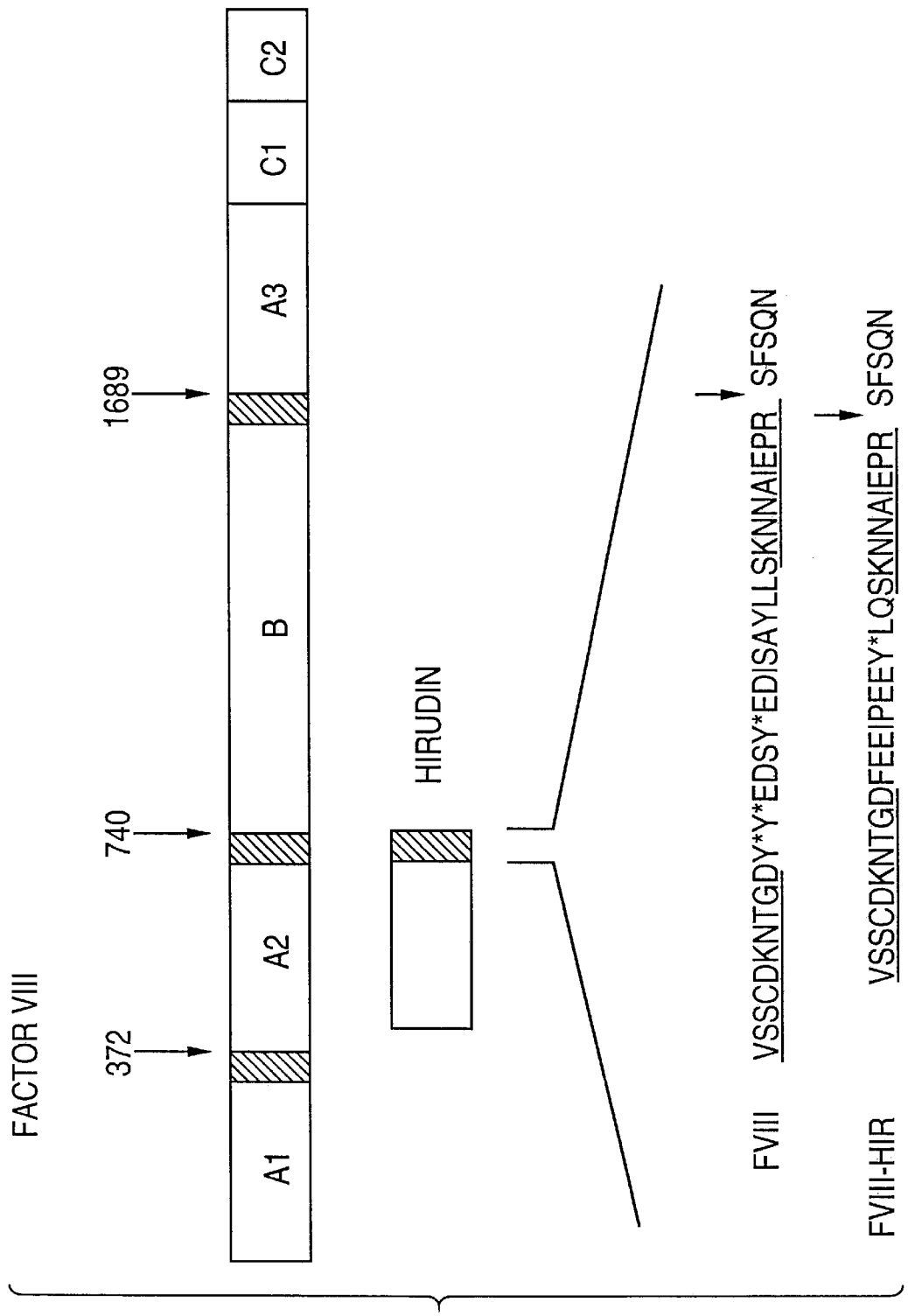
FIG. 6 is a schematic representation of the hybrid Factor VIII dB695-HIR. The domains of Factor VIII (A1-A2-B-A3-C1-C2) are interspersed by acidic regions as described in FIG. 1. In the lower section of the figure, the amino acid sequence of the region $Val^{708}$-$Ser^{746}$ of Factor VIII is depicted which contains an acidic region ($Ser^{710}$-$Arg^{740}$) and a cleavage site for thrombin at position $Arg^{740.}$ The sulfated tyrosines at amino acid position 718, 719 and 723 are indicated by asterisks. The sequence FVIII-HIR shows the corresponding region of the hybrid protein Factor VIII dB695-HIR. Amino acid sequences derived of the A2-domain of Factor VIII are underlined. The sulfated tyrosine obtained from the acidic region of hirudin is indicated by an asterisk (SEQ ID NOS: 15 and 17).

This example concerns the construction of a hybrid protein in which the amino acid sequence $Tyr^{718}$-$Ser^{732}$ of human Factor VIII has been replaced by amino acid sequence $Phe^{56}$-$Gln^{65}$ of hirudin. The sense primer SEQ ID NO 13 (5'-AGGAAATTCCAGAGGAATATTTGCAGA GTAAAAACAATGCCATT-3') and the antisense primer SEQ ID NO 12 (5'-GTCCCCACT GTGATGGAGC-3') were used to amplify a 371 bp fragment. The part of primer SEQ ID NO 13 that corresponds to hirudin is based upon the amino acid sequence of hirudin. Favorable codons have been selected for the different amino acids and a putative hirudin cDNA has been assembled. Part of the primers used for the construction of the Factor VIII-hirudin hybrid are based upon the putative hirudin cDNA sequence. The sense primer SEQ ID NO 11 and the antisense primer SEQ ID NO 14 (5'-AATATTCCTCTGGAATTTCCTCGAAAT CACCAGTGTTCTTGTC-3') were used to amplify a 502 bp fragment. Reaction conditions were: 2' 90° C., 20'50° C., 3'72° C., 37 times 45" 90° C., 90"50° C., 3'72° C., 5' 65° C. in the presence of 1 mM dNTPS, Pfu-polymerase reaction buffer, 50 pMol of sense primer and 50 pMol of antisense primer and 2.5 U of Pfu-polymerase (Stratagene, Cambridge, UK). Both the 502 bp and 371 bp fragment were purified by low-melting agarose, followed by phenol extraction and ethanol precipitation. Subsequently, 1 ng of each fragment was used as a template for the polymerase chain reaction employing primers SEQ ID NO 11 (5'-GTAGATCAAAGAGGAAACCAG-3') and SEQ ID NO 12. Reaction conditions were similar to that described above. The resulting fragment of 852 bp was digested with BamHI and HindIII, resulting in a 396 bp fragment which was used to replace the corresponding fragment of pCLB-dB695. Clones containing cDNA encoding the Factor VIII-hirudin hybrid protein were selected and the resulting plasmid was termed pCLB-dB695-HIR. The sequence of the 396 bp fragment that contained part of the putative hirudin cDNA was verified. FIG. 6 is a schematic representation of the resulting hybrid Factor VIII dB695-HIR protein that is encoded by the plasmid pCLB-dB695-HIR.

It is to be understood that the description, specific examples and data, while indicating preferred embodiments, are given by way of illustration and exemplification and are not intended to limit the present invention. Various changes and modifications within the present invention will become apparent to the skilled artisan from the discussion and disclosure contained herein.

---

What is claimed is:

1. A method of modifying a blood coagulation protein, comprising
replacing at least one acidic region of a Factor VIII protein with an acidic region from hirudin or heparin cofactor II.

2. A method of modifying a blood coagulation protein, replacing at least one acidic region of a Factor VIII mutant lacking part of the B-domain with an acidic region from hirudin or heparin cofactor II.

* * * * *

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
        ( A ) LENGTH: 5035 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 35..5017

( x i ) SEQUENCE DESCRIPTION: SEQ ID NO:1:

```
TCGACCTCCA GTTGAACATT TGTAGCAAGC CACC ATG GAA ATA GAG CTC TCC              52
                                     Met Glu Ile Glu Leu Ser
                                      1               5

ACC TGC TTC TTT CTG TGC CTT TTG CGA TTC TGC TTT AGT GCC ACC AGA           100
Thr Cys Phe Phe Leu Cys Leu Leu Arg Phe Cys Phe Ser Ala Thr Arg
         10                  15                  20

AGA TAC TAC CTG GGT GCA GTG GAA CTG TCA TGG GAC TAT ATG CAA AGT           148
Arg Tyr Tyr Leu Gly Ala Val Glu Leu Ser Trp Asp Tyr Met Gln Ser
         25                  30                  35

GAT CTC GGT GAG CTG CCT GTG GAC GCA AGA TTT CCT CCT AGA GTG CCA           196
Asp Leu Gly Glu Leu Pro Val Asp Ala Arg Phe Pro Pro Arg Val Pro
     40                  45                  50

AAA TCT TTT CCA TTC AAC ACC TCA GTC GTG TAC AAA AAG ACT CTG TTT           244
Lys Ser Phe Pro Phe Asn Thr Ser Val Val Tyr Lys Lys Thr Leu Phe
```

|  |  |  |  |  |  |  |  |  |  |  |  |  |  |  |  |  |
|---|---|---|---|---|---|---|---|---|---|---|---|---|---|---|---|---|
| 55 | | | | | 60 | | | | | 65 | | | | | 70 | |
| GTA | GAA | TTC | ACG | GAT | CAC | CTT | TTC | AAC | ATC | GCT | AAG | CCA | AGG | CCA | CCC | 292 |
| Val | Glu | Phe | Thr | Asp | His | Leu | Phe | Asn | Ile | Ala | Lys | Pro | Arg | Pro | Pro | |
| | | | | 75 | | | | | 80 | | | | | 85 | | |
| TGG | ATG | GGT | CTG | CTA | GGT | CCT | ACC | ATC | CAG | GCT | GAG | GTT | TAT | GAT | ACA | 340 |
| Trp | Met | Gly | Leu | Leu | Gly | Pro | Thr | Ile | Gln | Ala | Glu | Val | Tyr | Asp | Thr | |
| | | | 90 | | | | | 95 | | | | | 100 | | | |
| GTG | GTC | ATT | ACA | CTT | AAG | AAC | ATG | GCT | TCC | CAT | CCT | GTC | AGT | CTT | CAT | 388 |
| Val | Val | Ile | Thr | Leu | Lys | Asn | Met | Ala | Ser | His | Pro | Val | Ser | Leu | His | |
| | | 105 | | | | | 110 | | | | | 115 | | | | |
| GCT | GTT | GGT | GTA | TCC | TAC | TGG | AAA | GCT | TCT | GAG | GGA | GCT | GAA | TAT | GAT | 436 |
| Ala | Val | Gly | Val | Ser | Tyr | Trp | Lys | Ala | Ser | Glu | Gly | Ala | Glu | Tyr | Asp | |
| | | | 120 | | | | 125 | | | | | 130 | | | | |
| GAT | CAG | ACC | AGT | CAA | AGG | GAG | AAA | GAA | GAT | GAT | AAA | GTC | TTC | CCT | GGT | 484 |
| Asp | Gln | Thr | Ser | Gln | Arg | Glu | Lys | Glu | Asp | Asp | Lys | Val | Phe | Pro | Gly | |
| 135 | | | | | 140 | | | | | 145 | | | | | 150 | |
| GGA | AGC | CAT | ACA | TAT | GTC | TGG | CAG | GTC | CTG | AAA | GAG | AAT | GGT | CCA | ATG | 532 |
| Gly | Ser | His | Thr | Tyr | Val | Trp | Gln | Val | Leu | Lys | Glu | Asn | Gly | Pro | Met | |
| | | | | 155 | | | | | 160 | | | | | 165 | | |
| GCC | TCT | GAC | CCA | CTG | TGC | CTT | ACC | TAC | TCA | TAT | CTT | TCT | CAT | GTG | GAC | 580 |
| Ala | Ser | Asp | Pro | Leu | Cys | Leu | Thr | Tyr | Ser | Tyr | Leu | Ser | His | Val | Asp | |
| | | | 170 | | | | | 175 | | | | | 180 | | | |
| CTG | GTA | AAA | GAC | TTG | AAT | TCA | GGC | CTC | ATT | GGA | GCC | CTA | CTA | GTA | TGT | 628 |
| Leu | Val | Lys | Asp | Leu | Asn | Ser | Gly | Leu | Ile | Gly | Ala | Leu | Leu | Val | Cys | |
| | | 185 | | | | | 190 | | | | | 195 | | | | |
| AGA | GAA | GGG | AGT | CTG | GCC | AAG | GAA | AAG | ACA | CAG | ACC | TTG | CAC | AAA | TTT | 676 |
| Arg | Glu | Gly | Ser | Leu | Ala | Lys | Glu | Lys | Thr | Gln | Thr | Leu | His | Lys | Phe | |
| | | 200 | | | | | 205 | | | | | 210 | | | | |
| ATA | CTA | CTT | TTT | GCT | GTA | TTT | GAT | GAA | GGG | AAA | AGT | TGG | CAC | TCA | GAA | 724 |
| Ile | Leu | Leu | Phe | Ala | Val | Phe | Asp | Glu | Gly | Lys | Ser | Trp | His | Ser | Glu | |
| 215 | | | | | 220 | | | | | 225 | | | | | 230 | |
| ACA | AAG | AAC | TCC | TTG | ATG | CAG | GAT | AGG | GAT | GCT | GCA | TCT | GCT | CGG | GCC | 772 |
| Thr | Lys | Asn | Ser | Leu | Met | Gln | Asp | Arg | Asp | Ala | Ala | Ser | Ala | Arg | Ala | |
| | | | | 235 | | | | | 240 | | | | | 245 | | |
| TGG | CCT | AAA | ATG | CAC | ACA | GTC | AAT | GGT | TAT | GTA | AAC | AGG | TCT | CTG | CCA | 820 |
| Trp | Pro | Lys | Met | His | Thr | Val | Asn | Gly | Tyr | Val | Asn | Arg | Ser | Leu | Pro | |
| | | | 250 | | | | | 255 | | | | | 260 | | | |
| GGT | CTG | ATT | GGA | TGC | CAC | AGG | AAA | TCA | GTC | TAT | TGG | CAT | GTG | ATT | GGA | 868 |
| Gly | Leu | Ile | Gly | Cys | His | Arg | Lys | Ser | Val | Tyr | Trp | His | Val | Ile | Gly | |
| | | 265 | | | | | 270 | | | | | 275 | | | | |
| ATG | GGC | ACC | ACT | CCT | GAA | GTG | CAC | TCA | ATA | TTC | CTC | GAA | GGT | CAC | ACA | 916 |
| Met | Gly | Thr | Thr | Pro | Glu | Val | His | Ser | Ile | Phe | Leu | Glu | Gly | His | Thr | |
| | | 280 | | | | | 285 | | | | | 290 | | | | |
| TTT | CTT | GTG | AGG | AAC | CAT | CGC | CAG | GCG | TCC | TTG | GAA | ATC | TCG | CCA | ATA | 964 |
| Phe | Leu | Val | Arg | Asn | His | Arg | Gln | Ala | Ser | Leu | Glu | Ile | Ser | Pro | Ile | |
| 295 | | | | | 300 | | | | | 305 | | | | | 310 | |
| ACT | TTC | CTT | ACT | GCT | CAA | ACA | CTC | TTG | ATG | GAC | CTT | GGA | CAG | TTT | CTA | 1012 |
| Thr | Phe | Leu | Thr | Ala | Gln | Thr | Leu | Leu | Met | Asp | Leu | Gly | Gln | Phe | Leu | |
| | | | | 315 | | | | | 320 | | | | | 325 | | |
| CTG | TTT | TGT | CAT | ATC | TCT | TCC | CAC | CAA | CAT | GAT | GGC | ATG | GAA | GCT | TAT | 1060 |
| Leu | Phe | Cys | His | Ile | Ser | Ser | His | Gln | His | Asp | Gly | Met | Glu | Ala | Tyr | |
| | | | 330 | | | | | 335 | | | | | 340 | | | |
| GTC | AAA | GTA | GAC | AGC | TGT | CCA | GAG | GAA | CCC | CAA | CTA | CGA | ATG | AAA | AAT | 1108 |
| Val | Lys | Val | Asp | Ser | Cys | Pro | Glu | Glu | Pro | Gln | Leu | Arg | Met | Lys | Asn | |
| | | 345 | | | | | 350 | | | | | 355 | | | | |
| AAT | GAA | GAA | GCG | GAA | GAC | TAT | GAT | GAT | GAT | CTT | ACT | GAT | TCT | GAA | ATG | 1156 |
| Asn | Glu | Glu | Ala | Glu | Asp | Tyr | Asp | Asp | Asp | Leu | Thr | Asp | Ser | Glu | Met | |
| | 360 | | | | | 365 | | | | | 370 | | | | | |
| GAT | GTG | GTC | AGG | TTT | GAT | GAT | GAC | AAC | TCT | CCT | TCC | TTT | ATC | CAA | ATT | 1204 |
| Asp | Val | Val | Arg | Phe | Asp | Asp | Asp | Asn | Ser | Pro | Ser | Phe | Ile | Gln | Ile | |

```
375                         380                         385                         390
CGC  TCA  GTT  GCC  AAG  AAG  CAT  CCT  AAA  ACT  TGG  GTA  CAT  TAC  ATT  GCT       1252
Arg  Ser  Val  Ala  Lys  Lys  His  Pro  Lys  Thr  Trp  Val  His  Tyr  Ile  Ala
               395                      400                           405

GCT  GAA  GAG  GAG  GAC  TGG  GAC  TAT  GCT  CCC  TTA  GTC  CTC  GCC  CCC  GAT       1300
Ala  Glu  Glu  Glu  Asp  Trp  Asp  Tyr  Ala  Pro  Leu  Val  Leu  Ala  Pro  Asp
               410                      415                           420

GAC  AGA  AGT  TAT  AAA  AGT  CAA  TAT  TTG  AAC  AAT  GGC  CCT  CAG  CGG  ATT       1348
Asp  Arg  Ser  Tyr  Lys  Ser  Gln  Tyr  Leu  Asn  Asn  Gly  Pro  Gln  Arg  Ile
               425                      430                           435

GGT  AGG  AAG  TAC  AAA  AAA  GTC  CGA  TTT  ATG  GCA  TAC  ACA  GAT  GAA  ACC       1396
Gly  Arg  Lys  Tyr  Lys  Lys  Val  Arg  Phe  Met  Ala  Tyr  Thr  Asp  Glu  Thr
          440                      445                           450

TTT  AAG  ACT  CGT  GAA  GCT  ATT  CAG  CAT  GAA  TCA  GGA  ATC  TTG  GGA  CCT       1444
Phe  Lys  Thr  Arg  Glu  Ala  Ile  Gln  His  Glu  Ser  Gly  Ile  Leu  Gly  Pro
455                      460                      465                           470

TTA  CTT  TAT  GGG  GAA  GTT  GGA  GAC  ACA  CTG  TTG  ATT  ATA  TTT  AAG  AAT       1492
Leu  Leu  Tyr  Gly  Glu  Val  Gly  Asp  Thr  Leu  Leu  Ile  Ile  Phe  Lys  Asn
                    475                      480                           485

CAA  GCA  AGC  AGA  CCA  TAT  AAC  ATC  TAC  CCT  CAC  GGA  ATC  ACT  GAT  GTC       1540
Gln  Ala  Ser  Arg  Pro  Tyr  Asn  Ile  Tyr  Pro  His  Gly  Ile  Thr  Asp  Val
               490                      495                           500

CGT  CCT  TTG  TAT  TCA  AGG  AGA  TTA  CCA  AAA  GGT  GTA  AAA  CAT  TTG  AAG       1588
Arg  Pro  Leu  Tyr  Ser  Arg  Arg  Leu  Pro  Lys  Gly  Val  Lys  His  Leu  Lys
          505                      510                           515

GAT  TTT  CCA  ATT  CTG  CCA  GGA  GAA  ATA  TTC  AAA  TAT  AAA  TGG  ACA  GTG       1636
Asp  Phe  Pro  Ile  Leu  Pro  Gly  Glu  Ile  Phe  Lys  Tyr  Lys  Trp  Thr  Val
     520                      525                           530

ACT  GTA  GAA  GAT  GGG  CCA  ACT  AAA  TCA  GAT  CCT  CGG  TGC  CTG  ACC  CGC       1684
Thr  Val  Glu  Asp  Gly  Pro  Thr  Lys  Ser  Asp  Pro  Arg  Cys  Leu  Thr  Arg
535                      540                      545                           550

TAT  TAC  TCT  AGT  TTC  GTT  AAT  ATG  GAG  AGA  GAT  CTA  GCT  TCA  GGA  CTC       1732
Tyr  Tyr  Ser  Ser  Phe  Val  Asn  Met  Glu  Arg  Asp  Leu  Ala  Ser  Gly  Leu
                    555                      560                           565

ATT  GGC  CCT  CTC  CTC  ATC  TGC  TAC  AAA  GAA  TCT  GTA  GAT  CAA  AGA  GGA       1780
Ile  Gly  Pro  Leu  Leu  Ile  Cys  Tyr  Lys  Glu  Ser  Val  Asp  Gln  Arg  Gly
               570                      575                           580

AAC  CAG  ATA  ATG  TCA  GAC  AAG  AGG  AAT  GTC  ATC  CTG  TTT  TCT  GTA  TTT       1828
Asn  Gln  Ile  Met  Ser  Asp  Lys  Arg  Asn  Val  Ile  Leu  Phe  Ser  Val  Phe
          585                      590                           595

GAT  GAG  AAC  CGA  AGC  TGG  TAC  CTC  ACA  GAG  AAT  ATA  CAA  CGC  TTT  CTC       1876
Asp  Glu  Asn  Arg  Ser  Trp  Tyr  Leu  Thr  Glu  Asn  Ile  Gln  Arg  Phe  Leu
     600                      605                           610

CCC  AAT  CCA  GCT  GGA  GTG  CAG  CTT  GAG  GAT  CCA  GAG  TTC  CAA  GCC  TCC       1924
Pro  Asn  Pro  Ala  Gly  Val  Gln  Leu  Glu  Asp  Pro  Glu  Phe  Gln  Ala  Ser
615                      620                      625                           630

AAC  ATC  ATG  CAC  AGC  ATC  AAT  GGC  TAT  GTT  TTT  GAT  AGT  TTG  CAG  TTG       1972
Asn  Ile  Met  His  Ser  Ile  Asn  Gly  Tyr  Val  Phe  Asp  Ser  Leu  Gln  Leu
                    635                      640                           645

TCA  GTT  TGT  TTG  CAT  GAG  GTG  GCA  TAC  TGG  TAC  ATT  CTA  AGC  ATT  GGA       2020
Ser  Val  Cys  Leu  His  Glu  Val  Ala  Tyr  Trp  Tyr  Ile  Leu  Ser  Ile  Gly
               650                      655                           660

GCA  CAG  ACT  GAC  TTC  CTT  TCT  GTC  TTC  TTC  TCT  GGA  TAT  ACC  TTC  AAA       2068
Ala  Gln  Thr  Asp  Phe  Leu  Ser  Val  Phe  Phe  Ser  Gly  Tyr  Thr  Phe  Lys
          665                      670                           675

CAC  AAA  ATG  GTC  TAT  GAA  GAC  ACA  CTC  ACC  CTA  TTC  CCA  TTC  TCA  GGA       2116
His  Lys  Met  Val  Tyr  Glu  Asp  Thr  Leu  Thr  Leu  Phe  Pro  Phe  Ser  Gly
     680                      685                           690

GAA  ACT  GTC  TTC  ATG  TCG  ATG  GAA  AAC  CCA  GGT  CTA  TGG  ATT  CTG  GGG       2164
Glu  Thr  Val  Phe  Met  Ser  Met  Glu  Asn  Pro  Gly  Leu  Trp  Ile  Leu  Gly
```

|     |     |     |     |     |     |     |     |     |     |     |     |     |     |     |     |
| --- | --- | --- | --- | --- | --- | --- | --- | --- | --- | --- | --- | --- | --- | --- | --- |
| 695 |     |     |     |     |     | 700 |     |     |     |     | 705 |     |     |     | 710 |

| TGC | CAC | AAC | TCA | GAC | TTT | CGG | AAC | AGA | GGC | ATG | ACC | GCC | TTA | CTG | AAG | 2212 |
| --- | --- | --- | --- | --- | --- | --- | --- | --- | --- | --- | --- | --- | --- | --- | --- | --- |
| Cys | His | Asn | Ser | Asp | Phe | Arg | Asn | Arg | Gly | Met | Thr | Ala | Leu | Leu | Lys | |
| 715 | | | | | | | 720 | | | | | | 725 | | | |

| GTT | TCT | AGT | TGT | ATT | CCA | GAG | GGG | GAG | GAG | GAC | GAC | GAC | TAT | CTG | GAC | 2260 |
| Val | Ser | Ser | Cys | Ile | Pro | Glu | Gly | Glu | Glu | Asp | Asp | Asp | Tyr | Leu | Asp | |
| | | | 730 | | | | | 735 | | | | | 740 | | | |

| CTG | GAG | AAG | ATA | TTC | AGT | GAA | GAC | GAC | GAC | TAC | ATC | GAC | ATC | GTC | GAC | 2308 |
| Leu | Glu | Lys | Ile | Phe | Ser | Glu | Asp | Asp | Asp | Tyr | Ile | Asp | Ile | Val | Asp | |
| | | 745 | | | | | 750 | | | | | 755 | | | | |

| AGT | CTG | ATT | GAA | CCA | AGA | AGC | TTC | TCC | CAG | AAT | TCA | AGA | CAC | CCT | AGC | 2356 |
| Ser | Leu | Ile | Glu | Pro | Arg | Ser | Phe | Ser | Gln | Asn | Ser | Arg | His | Pro | Ser | |
| | 760 | | | | | 765 | | | | | 770 | | | | | |

| ACT | AGG | CAA | AAG | CAA | TTT | AAT | GCC | ACC | ACA | ATT | CCA | GAA | AAT | GAC | ATA | 2404 |
| Thr | Arg | Gln | Lys | Gln | Phe | Asn | Ala | Thr | Thr | Ile | Pro | Glu | Asn | Asp | Ile | |
| 775 | | | | | 780 | | | | | 785 | | | | | 790 | |

| GAG | AAG | ACT | GAC | CCT | TGG | TTT | GCA | CAC | AGA | ACA | CCT | ATG | CCT | AAA | ATA | 2452 |
| Glu | Lys | Thr | Asp | Pro | Trp | Phe | Ala | His | Arg | Thr | Pro | Met | Pro | Lys | Ile | |
| | | | | 795 | | | | | 800 | | | | | 805 | | |

| CAA | AAT | GTC | TCC | TCT | AGT | GAT | TTG | TTG | ATG | CTC | TTG | CGA | CAG | AGT | CCT | 2500 |
| Gln | Asn | Val | Ser | Ser | Ser | Asp | Leu | Leu | Met | Leu | Leu | Arg | Gln | Ser | Pro | |
| | | | 810 | | | | | 815 | | | | | 820 | | | |

| ACT | CCA | CAT | GGG | CTA | TCC | TTA | TCT | GAT | CTC | CAA | GAA | GCC | AAA | TAT | GAG | 2548 |
| Thr | Pro | His | Gly | Leu | Ser | Leu | Ser | Asp | Leu | Gln | Glu | Ala | Lys | Tyr | Glu | |
| | | 825 | | | | | 830 | | | | | 835 | | | | |

| ACT | TTT | TCT | GAT | GAT | CCA | TCA | CCT | GGA | GCA | ATA | GAC | AGT | AAT | AAC | AGC | 2596 |
| Thr | Phe | Ser | Asp | Asp | Pro | Ser | Pro | Gly | Ala | Ile | Asp | Ser | Asn | Asn | Ser | |
| | 840 | | | | | 845 | | | | | 850 | | | | | |

| CTG | TCT | GAA | ATG | ACA | CAC | TTC | AGG | CCA | CAG | CTC | CAT | CAC | AGT | GGG | GAC | 2644 |
| Leu | Ser | Glu | Met | Thr | His | Phe | Arg | Pro | Gln | Leu | His | His | Ser | Gly | Asp | |
| 855 | | | | | 860 | | | | | 865 | | | | | 870 | |

| ATG | GTA | TTT | ACC | CCT | GAG | TCA | GGC | CTC | CAA | TTA | AGA | TTA | AAT | GAG | AAA | 2692 |
| Met | Val | Phe | Thr | Pro | Glu | Ser | Gly | Leu | Gln | Leu | Arg | Leu | Asn | Glu | Lys | |
| | | | | 875 | | | | | 880 | | | | | 885 | | |

| CTG | GGG | ACA | ACT | GCA | GAT | CCT | CTT | GCT | TGG | GAT | AAC | CAC | TAT | GGT | ACT | 2740 |
| Leu | Gly | Thr | Thr | Ala | Asp | Pro | Leu | Ala | Trp | Asp | Asn | His | Tyr | Gly | Thr | |
| | | | 890 | | | | | 895 | | | | | 900 | | | |

| CAG | ATA | CCA | AAA | GAA | GAG | TGG | AAA | TCC | CAA | GAG | AAG | TCA | CCA | GAA | AAA | 2788 |
| Gln | Ile | Pro | Lys | Glu | Glu | Trp | Lys | Ser | Gln | Glu | Lys | Ser | Pro | Glu | Lys | |
| | | 905 | | | | | 910 | | | | | 915 | | | | |

| ACA | GCT | TTT | AAG | AAA | AAG | GAT | ACC | ATT | TTG | TCC | CTG | AAC | GCT | TGT | GAA | 2836 |
| Thr | Ala | Phe | Lys | Lys | Lys | Asp | Thr | Ile | Leu | Ser | Leu | Asn | Ala | Cys | Glu | |
| | 920 | | | | | 925 | | | | | 930 | | | | | |

| AGC | AAT | CAT | GCA | ATA | GCA | GCA | ATA | AAT | GAG | GGA | CAA | AAT | AAG | CCC | GAA | 2884 |
| Ser | Asn | His | Ala | Ile | Ala | Ala | Ile | Asn | Glu | Gly | Gln | Asn | Lys | Pro | Glu | |
| 935 | | | | 940 | | | | | 945 | | | | | 950 | | |

| ATA | GAA | GTC | ACC | TGG | GCA | AAG | CAA | GGT | AGG | ACT | GAA | AGG | CTG | TGC | TCT | 2932 |
| Ile | Glu | Val | Thr | Trp | Ala | Lys | Gln | Gly | Arg | Thr | Glu | Arg | Leu | Cys | Ser | |
| | | | | 955 | | | | | 960 | | | | | 965 | | |

| CAA | AAC | CCA | CCA | GTC | TTG | AAA | CGC | CAT | CAA | CGG | GAA | ATA | ACT | CGT | ACT | 2980 |
| Gln | Asn | Pro | Pro | Val | Leu | Lys | Arg | His | Gln | Arg | Glu | Ile | Thr | Arg | Thr | |
| | | | 970 | | | | | 975 | | | | | 980 | | | |

| ACT | CTT | CAG | TCA | GAT | CAA | GAG | GAA | ATT | GAC | TAT | GAT | GAT | ACC | ATA | TCA | 3028 |
| Thr | Leu | Gln | Ser | Asp | Gln | Glu | Glu | Ile | Asp | Tyr | Asp | Asp | Thr | Ile | Ser | |
| | | 985 | | | | | 990 | | | | | 995 | | | | |

| GTT | GAA | ATG | AAG | AAG | GAA | GAT | TTT | GAC | ATT | TAT | GAT | GAG | GAT | GAA | AAT | 3076 |
| Val | Glu | Met | Lys | Lys | Glu | Asp | Phe | Asp | Ile | Tyr | Asp | Glu | Asp | Glu | Asn | |
| | | 1000 | | | | | 1005 | | | | | 1010 | | | | |

| CAG | AGC | CCC | CGC | AGC | TTT | CAA | AAG | AAA | ACA | CGA | CAC | TAT | TTT | ATT | GCT | 3124 |
| Gln | Ser | Pro | Arg | Ser | Phe | Gln | Lys | Lys | Thr | Arg | His | Tyr | Phe | Ile | Ala | |

-continued

| | | | | | | | | | | | | | | | | |
|---|---|---|---|---|---|---|---|---|---|---|---|---|---|---|---|---|
| | 1015 | | | | | 1020 | | | | | 1025 | | | | | 1030 |

```
GCA  GTG  GAG  AGG  CTC  TGG  GAT  TAT  GGG  ATG  AGT  AGC  TCC  CCA  CAT  GTT         3172
Ala  Val  Glu  Arg  Leu  Trp  Asp  Tyr  Gly  Met  Ser  Ser  Ser  Pro  His  Val
               1035                         1040                      1045

CTA  AGA  AAC  AGG  GCT  CAG  AGT  GGC  AGT  GTC  CCT  CAG  TTC  AAG  AAA  GTT         3220
Leu  Arg  Asn  Arg  Ala  Gln  Ser  Gly  Ser  Val  Pro  Gln  Phe  Lys  Lys  Val
               1050                         1055                      1060

GTT  TTC  CAG  GAA  TTT  ACT  GAT  GGC  TCC  TTT  ACT  CAG  CCC  TTA  TAC  CGT         3268
Val  Phe  Gln  Glu  Phe  Thr  Asp  Gly  Ser  Phe  Thr  Gln  Pro  Leu  Tyr  Arg
               1065                         1070                      1075

GGA  GAA  CTA  AAT  GAA  CAT  TTG  GGA  CTC  CTG  GGG  CCA  TAT  ATA  AGA  GCA         3316
Gly  Glu  Leu  Asn  Glu  His  Leu  Gly  Leu  Leu  Gly  Pro  Tyr  Ile  Arg  Ala
          1080                         1085                      1090

GAA  GTT  GAA  GAT  AAT  ATC  ATG  GTA  ACT  TTC  AGA  AAT  CAG  GCC  TCT  CGT         3364
Glu  Val  Glu  Asp  Asn  Ile  Met  Val  Thr  Phe  Arg  Asn  Gln  Ala  Ser  Arg
1095                         1100                      1105                      1110

CCC  TAT  TCC  TTC  TAT  TCT  AGC  CTT  ATT  TCT  TAT  GAG  GAA  GAT  CAG  AGG         3412
Pro  Tyr  Ser  Phe  Tyr  Ser  Ser  Leu  Ile  Ser  Tyr  Glu  Glu  Asp  Gln  Arg
                    1115                         1120                      1125

CAA  GGA  GCA  GAA  CCT  AGA  AAA  AAC  TTT  GTC  AAG  CCT  AAT  GAA  ACC  AAA         3460
Gln  Gly  Ala  Glu  Pro  Arg  Lys  Asn  Phe  Val  Lys  Pro  Asn  Glu  Thr  Lys
               1130                         1135                      1140

ACT  TAC  TTT  TGG  AAA  GTG  CAA  CAT  CAT  ATG  GCA  CCC  ACT  AAA  GAT  GAG         3508
Thr  Tyr  Phe  Trp  Lys  Val  Gln  His  His  Met  Ala  Pro  Thr  Lys  Asp  Glu
               1145                         1150                      1155

TTT  GAC  TGC  AAA  GCC  TGG  GCT  TAT  TTC  TCT  GAT  GTT  GAC  CTG  GAA  AAA         3556
Phe  Asp  Cys  Lys  Ala  Trp  Ala  Tyr  Phe  Ser  Asp  Val  Asp  Leu  Glu  Lys
               1160                         1165                      1170

GAT  GTG  CAC  TCA  GGC  CTG  ATT  GGA  CCC  CTT  CTG  GTC  TGC  CAC  ACT  AAC         3604
Asp  Val  His  Ser  Gly  Leu  Ile  Gly  Pro  Leu  Leu  Val  Cys  His  Thr  Asn
1175                         1180                      1185                      1190

ACA  CTG  AAC  CCT  GCT  CAT  GGG  AGA  CAA  GTG  ACA  GTA  CAG  GAA  TTT  GCT         3652
Thr  Leu  Asn  Pro  Ala  His  Gly  Arg  Gln  Val  Thr  Val  Gln  Glu  Phe  Ala
                         1195                         1200                      1205

CTG  TTT  TTC  ACC  ATC  TTT  GAT  GAG  ACC  AAA  AGC  TGG  TAC  TTC  ACT  GAA         3700
Leu  Phe  Phe  Thr  Ile  Phe  Asp  Glu  Thr  Lys  Ser  Trp  Tyr  Phe  Thr  Glu
               1210                         1215                      1220

AAT  ATG  GAA  AGA  AAC  TGC  AGG  GCT  CCC  TGC  AAT  ATC  CAG  ATG  GAA  GAT         3748
Asn  Met  Glu  Arg  Asn  Cys  Arg  Ala  Pro  Cys  Asn  Ile  Gln  Met  Glu  Asp
               1225                         1230                      1235

CCC  ACT  TTT  AAA  GAG  AAT  TAT  CGC  TTC  CAT  GCA  ATC  AAT  GGC  TAC  ATA         3796
Pro  Thr  Phe  Lys  Glu  Asn  Tyr  Arg  Phe  His  Ala  Ile  Asn  Gly  Tyr  Ile
     1240                         1245                      1250

ATG  GAT  ACA  CTA  CCT  GGC  TTA  GTA  ATG  GCT  CAG  GAT  CAA  AGG  ATT  CGA         3844
Met  Asp  Thr  Leu  Pro  Gly  Leu  Val  Met  Ala  Gln  Asp  Gln  Arg  Ile  Arg
1255                         1260                      1265                      1270

TGG  TAT  CTG  CTC  AGC  ATG  GGC  AGC  AAT  GAA  AAC  ATC  CAT  TCT  ATT  CAT         3892
Trp  Tyr  Leu  Leu  Ser  Met  Gly  Ser  Asn  Glu  Asn  Ile  His  Ser  Ile  His
                    1275                         1280                      1285

TTC  AGT  GGA  CAT  GTG  TTC  ACT  GTA  CGA  AAA  AAA  GAG  GAG  TAT  AAA  ATG         3940
Phe  Ser  Gly  His  Val  Phe  Thr  Val  Arg  Lys  Lys  Glu  Glu  Tyr  Lys  Met
               1290                         1295                      1300

GCA  CTG  TAC  AAT  CTC  TAT  CCA  GGT  GTT  TTT  GAG  ACA  GTG  GAA  ATG  TTA         3988
Ala  Leu  Tyr  Asn  Leu  Tyr  Pro  Gly  Val  Phe  Glu  Thr  Val  Glu  Met  Leu
               1305                         1310                      1315

CCA  TCC  AAA  GCT  GGA  ATT  TGG  CGG  GTG  GAA  TGC  CTT  ATT  GGC  GAG  CAT         4036
Pro  Ser  Lys  Ala  Gly  Ile  Trp  Arg  Val  Glu  Cys  Leu  Ile  Gly  Glu  His
               1320                         1325                      1330

CTA  CAT  GCT  GGG  ATG  AGC  ACA  CTT  TTT  CTG  GTG  TAC  AGC  AAT  AAG  TGT         4084
Leu  His  Ala  Gly  Met  Ser  Thr  Leu  Phe  Leu  Val  Tyr  Ser  Asn  Lys  Cys
```

```
                    1335                      1340                      1345                      1350

CAG  ACT  CCC  CTG  GGA  ATG  GCT  TCT  GGA  CAC  ATT  AGA  GAT  TTT  CAG  ATT           4132
Gln  Thr  Pro  Leu  Gly  Met  Ala  Ser  Gly  His  Ile  Arg  Asp  Phe  Gln  Ile
                    1355                     1360                     1365

ACA  GCT  TCA  GGA  CAA  TAT  GGA  CAG  TGG  GCC  CCA  AAG  CTG  GCC  AGA  CTT           4180
Thr  Ala  Ser  Gly  Gln  Tyr  Gly  Gln  Trp  Ala  Pro  Lys  Leu  Ala  Arg  Leu
                    1370                     1375                     1380

CAT  TAT  TCC  GGA  TCA  ATC  AAT  GCC  TGG  AGC  ACC  AAG  GAG  CCC  TTT  TCT           4228
His  Tyr  Ser  Gly  Ser  Ile  Asn  Ala  Trp  Ser  Thr  Lys  Glu  Pro  Phe  Ser
                    1385                     1390                     1395

TGG  ATC  AAG  GTG  GAT  CTG  TTG  GCA  CCA  ATG  ATT  ATT  CAC  GGC  ATC  AAG           4276
Trp  Ile  Lys  Val  Asp  Leu  Leu  Ala  Pro  Met  Ile  Ile  His  Gly  Ile  Lys
     1400                     1405                     1410

ACC  CAG  GGT  GCC  CGT  CAG  AAG  TTC  TCC  AGC  CTC  TAC  ATC  TCT  CAG  TTT           4324
Thr  Gln  Gly  Ala  Arg  Gln  Lys  Phe  Ser  Ser  Leu  Tyr  Ile  Ser  Gln  Phe
1415                     1420                     1425                     1430

ATC  ATC  ATG  TAT  AGT  CTT  GAT  GGG  AAG  AAG  TGG  CAG  ACT  TAT  CGA  GGA           4372
Ile  Ile  Met  Tyr  Ser  Leu  Asp  Gly  Lys  Lys  Trp  Gln  Thr  Tyr  Arg  Gly
                    1435                     1440                     1445

AAT  TCC  ACT  GGA  ACC  TTA  ATG  GTC  TTC  TTT  GGC  AAT  GTG  GAT  TCA  TCT           4420
Asn  Ser  Thr  Gly  Thr  Leu  Met  Val  Phe  Phe  Gly  Asn  Val  Asp  Ser  Ser
                    1450                     1455                     1460

GGG  ATA  AAA  CAC  AAT  ATT  TTT  AAC  CCT  CCA  ATT  ATT  GCT  CGA  TAC  ATC           4468
Gly  Ile  Lys  His  Asn  Ile  Phe  Asn  Pro  Pro  Ile  Ile  Ala  Arg  Tyr  Ile
                    1465                     1470                     1475

CGT  TTG  CAC  CCA  ACT  CAT  TAT  AGC  ATT  CGC  AGC  ACT  CTT  CGC  ATG  GAG           4516
Arg  Leu  His  Pro  Thr  His  Tyr  Ser  Ile  Arg  Ser  Thr  Leu  Arg  Met  Glu
                    1480                     1485                     1490

TTG  ATG  GGC  TGT  GAT  TTA  AAT  AGT  TGC  AGC  ATG  CCA  TTG  GGA  ATG  GAG           4564
Leu  Met  Gly  Cys  Asp  Leu  Asn  Ser  Cys  Ser  Met  Pro  Leu  Gly  Met  Glu
1495                     1500                     1505                     1510

AGT  AAA  GCA  ATA  TCA  GAT  GCA  CAG  ATT  ACT  GCT  TCA  TCC  TAC  TTT  ACC           4612
Ser  Lys  Ala  Ile  Ser  Asp  Ala  Gln  Ile  Thr  Ala  Ser  Ser  Tyr  Phe  Thr
                    1515                     1520                     1525

AAT  ATG  TTT  GCC  ACC  TGG  TCT  CCT  TCA  AAA  GCT  CGA  CTT  CAC  CTC  CAA           4660
Asn  Met  Phe  Ala  Thr  Trp  Ser  Pro  Ser  Lys  Ala  Arg  Leu  His  Leu  Gln
                    1530                     1535                     1540

GGG  AGG  AGT  AAT  GCC  TGG  AGA  CCT  CAG  GTG  AAT  AAT  CCA  AAA  GAG  TGG           4708
Gly  Arg  Ser  Asn  Ala  Trp  Arg  Pro  Gln  Val  Asn  Asn  Pro  Lys  Glu  Trp
                    1545                     1550                     1555

CTG  CAA  GTG  GAC  TTC  CAG  AAG  ACA  ATG  AAA  GTC  ACA  GGA  GTA  ACT  ACT           4756
Leu  Gln  Val  Asp  Phe  Gln  Lys  Thr  Met  Lys  Val  Thr  Gly  Val  Thr  Thr
                    1560                     1565                     1570

CAG  GGA  GTA  AAA  TCT  CTG  CTT  ACC  AGC  ATG  TAT  GTG  AAG  GAG  TTC  CTC           4804
Gln  Gly  Val  Lys  Ser  Leu  Leu  Thr  Ser  Met  Tyr  Val  Lys  Glu  Phe  Leu
1575                     1580                     1585                     1590

ATC  TCC  AGC  AGT  CAA  GAT  GGC  CAT  CAG  TGG  ACT  CTC  TTT  TTT  CAG  AAT           4852
Ile  Ser  Ser  Ser  Gln  Asp  Gly  His  Gln  Trp  Thr  Leu  Phe  Phe  Gln  Asn
                    1595                     1600                     1605

GGC  AAA  GTA  AAG  GTT  TTT  CAG  GGA  AAT  CAA  GAC  TCC  TTC  ACA  CCT  GTG           4900
Gly  Lys  Val  Lys  Val  Phe  Gln  Gly  Asn  Gln  Asp  Ser  Phe  Thr  Pro  Val
                    1610                     1615                     1620

GTG  AAC  TCT  CTA  GAC  CCA  CCG  TTA  CTG  ACT  CGC  TAC  CTT  CGA  ATT  CAC           4948
Val  Asn  Ser  Leu  Asp  Pro  Pro  Leu  Leu  Thr  Arg  Tyr  Leu  Arg  Ile  His
                    1625                     1630                     1635

CCC  CAG  AGT  TGG  GTG  CAC  CAG  ATT  GCC  CTG  AGG  ATG  GAG  GTT  CTG  GGC           4996
Pro  Gln  Ser  Trp  Val  His  Gln  Ile  Ala  Leu  Arg  Met  Glu  Val  Leu  Gly
                    1640                     1645                     1650

TGC  GAG  GCA  CAG  GAC  CTC  TAC  TGAGGGTGGC  CACTGCAG                                    5035
Cys  Glu  Ala  Gln  Asp  Leu  Tyr
```

1655 1660

(2) INFORMATION FOR SEQ ID NO:2:

(i) SEQUENCE CHARACTERISTICS:
        (A) LENGTH: 1661 amino acids
        (B) TYPE: amino acid
        (D) TOPOLOGY: linear (ii) MOLECULE TYPE: protein (xi) SEQUENCE DESCRIPTION: SEQ ID NO:2:

```
Met Glu Ile Glu Leu Ser Thr Cys Phe Phe Leu Cys Leu Leu Arg Phe
 1               5                  10                  15

Cys Phe Ser Ala Thr Arg Arg Tyr Tyr Leu Gly Ala Val Glu Leu Ser
             20                  25                  30

Trp Asp Tyr Met Gln Ser Asp Leu Gly Glu Leu Pro Val Asp Ala Arg
                 35                  40                  45

Phe Pro Pro Arg Val Pro Lys Ser Phe Pro Phe Asn Thr Ser Val Val
         50                  55                  60

Tyr Lys Lys Thr Leu Phe Val Glu Phe Thr Asp His Leu Phe Asn Ile
 65                  70                  75                  80

Ala Lys Pro Arg Pro Pro Trp Met Gly Leu Leu Gly Pro Thr Ile Gln
                     85                  90                  95

Ala Glu Val Tyr Asp Thr Val Val Ile Thr Leu Lys Asn Met Ala Ser
                100                 105                 110

His Pro Val Ser Leu His Ala Val Gly Val Ser Tyr Trp Lys Ala Ser
             115                 120                 125

Glu Gly Ala Glu Tyr Asp Asp Gln Thr Ser Gln Arg Glu Lys Glu Asp
130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
             180                 185                 190

Gly Ala Leu Leu Val Cys Arg Glu Gly Ser Leu Ala Lys Glu Lys Thr
            195                 200                 205

Gln Thr Leu His Lys Phe Ile Leu Leu Phe Ala Val Phe Asp Glu Gly
210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
             260                 265                 270

Tyr Trp His Val Ile Gly Met Gly Thr Thr Pro Glu Val His Ser Ile
            275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350
```

-continued

| | | | | | | | | | | | | | | |
|---|---|---|---|---|---|---|---|---|---|---|---|---|---|---|
| Gln | Leu | Arg | Met | Lys | Asn | Asn | Glu | Glu | Ala | Glu | Asp | Tyr | Asp | Asp |
| | | 355 | | | | 360 | | | | | 365 | | | |
| Leu | Thr | Asp | Ser | Glu | Met | Asp | Val | Val | Arg | Phe | Asp | Asp | Asn | Ser |
| | 370 | | | | | 375 | | | | 380 | | | | |
| Pro | Ser | Phe | Ile | Gln | Ile | Arg | Ser | Val | Ala | Lys | His | Pro | Lys | Thr |
| 385 | | | | | 390 | | | | | 395 | | | | 400 |
| Trp | Val | His | Tyr | Ile | Ala | Ala | Glu | Glu | Asp | Trp | Asp | Tyr | Ala | Pro |
| | | | | 405 | | | | | 410 | | | | 415 | |
| Leu | Val | Leu | Ala | Pro | Asp | Asp | Arg | Ser | Tyr | Lys | Ser | Gln | Tyr | Leu | Asn |
| | | | 420 | | | | | 425 | | | | | 430 | | |
| Asn | Gly | Pro | Gln | Arg | Ile | Gly | Arg | Lys | Tyr | Lys | Lys | Val | Arg | Phe | Met |
| | | 435 | | | | | 440 | | | | | 445 | | | |
| Ala | Tyr | Thr | Asp | Glu | Thr | Phe | Lys | Thr | Arg | Glu | Ala | Ile | Gln | His | Glu |
| | 450 | | | | | | 455 | | | | | 460 | | | |
| Ser | Gly | Ile | Leu | Gly | Pro | Leu | Leu | Tyr | Gly | Glu | Val | Gly | Asp | Thr | Leu |
| 465 | | | | | 470 | | | | | 475 | | | | | 480 |
| Leu | Ile | Ile | Phe | Lys | Asn | Gln | Ala | Ser | Arg | Pro | Tyr | Asn | Ile | Tyr | Pro |
| | | | | 485 | | | | | 490 | | | | | 495 | |
| His | Gly | Ile | Thr | Asp | Val | Arg | Pro | Leu | Tyr | Ser | Arg | Arg | Leu | Pro | Lys |
| | | | 500 | | | | | 505 | | | | | 510 | | |
| Gly | Val | Lys | His | Leu | Lys | Asp | Phe | Pro | Ile | Leu | Pro | Gly | Glu | Ile | Phe |
| | | 515 | | | | | 520 | | | | | 525 | | | |
| Lys | Tyr | Lys | Trp | Thr | Val | Thr | Val | Glu | Asp | Gly | Pro | Thr | Lys | Ser | Asp |
| | 530 | | | | | 535 | | | | | 540 | | | | |
| Pro | Arg | Cys | Leu | Thr | Arg | Tyr | Tyr | Ser | Ser | Phe | Val | Asn | Met | Glu | Arg |
| 545 | | | | | 550 | | | | | 555 | | | | | 560 |
| Asp | Leu | Ala | Ser | Gly | Leu | Ile | Gly | Pro | Leu | Leu | Ile | Cys | Tyr | Lys | Glu |
| | | | | 565 | | | | | 570 | | | | | 575 | |
| Ser | Val | Asp | Gln | Arg | Gly | Asn | Gln | Ile | Met | Ser | Asp | Lys | Arg | Asn | Val |
| | | | 580 | | | | | 585 | | | | | 590 | | |
| Ile | Leu | Phe | Ser | Val | Phe | Asp | Glu | Asn | Arg | Ser | Trp | Tyr | Leu | Thr | Glu |
| | | | 595 | | | | | 600 | | | | | 605 | | |
| Asn | Ile | Gln | Arg | Phe | Leu | Pro | Asn | Pro | Ala | Gly | Val | Gln | Leu | Glu | Asp |
| | 610 | | | | | 615 | | | | | 620 | | | | |
| Pro | Glu | Phe | Gln | Ala | Ser | Asn | Ile | Met | His | Ser | Ile | Asn | Gly | Tyr | Val |
| 625 | | | | | 630 | | | | | 635 | | | | | 640 |
| Phe | Asp | Ser | Leu | Gln | Leu | Ser | Val | Cys | Leu | His | Glu | Val | Ala | Tyr | Trp |
| | | | | 645 | | | | | 650 | | | | | 655 | |
| Tyr | Ile | Leu | Ser | Ile | Gly | Ala | Gln | Thr | Asp | Phe | Leu | Ser | Val | Phe | Phe |
| | | | 660 | | | | | 665 | | | | | 670 | | |
| Ser | Gly | Tyr | Thr | Phe | Lys | His | Lys | Met | Val | Tyr | Glu | Asp | Thr | Leu | Thr |
| | | 675 | | | | | 680 | | | | | 685 | | | |
| Leu | Phe | Pro | Phe | Ser | Gly | Glu | Thr | Val | Phe | Met | Ser | Met | Glu | Asn | Pro |
| | 690 | | | | | 695 | | | | | 700 | | | | |
| Gly | Leu | Trp | Ile | Leu | Gly | Cys | His | Asn | Ser | Asp | Phe | Arg | Asn | Arg | Gly |
| 705 | | | | | 710 | | | | | 715 | | | | | 720 |
| Met | Thr | Ala | Leu | Leu | Lys | Val | Ser | Ser | Cys | Ile | Pro | Glu | Gly | Glu | Glu |
| | | | | 725 | | | | | 730 | | | | | 735 | |
| Asp | Asp | Asp | Tyr | Leu | Asp | Leu | Glu | Lys | Ile | Phe | Ser | Glu | Asp | Asp |
| | | | 740 | | | | | 745 | | | | | 750 | |
| Tyr | Ile | Asp | Ile | Val | Asp | Ser | Leu | Ile | Glu | Pro | Arg | Ser | Phe | Ser | Gln |
| | | 755 | | | | | 760 | | | | | 765 | | | |
| Asn | Ser | Arg | His | Pro | Ser | Thr | Arg | Gln | Lys | Gln | Phe | Asn | Ala | Thr | Thr |
| | | 770 | | | | | 775 | | | | | 780 | | | |

-continued

```
Ile  Pro  Glu  Asn  Asp  Ile  Glu  Lys  Thr  Asp  Pro  Trp  Phe  Ala  His  Arg
785            790                 795                      800

Thr  Pro  Met  Pro  Lys  Ile  Gln  Asn  Val  Ser  Ser  Ser  Asp  Leu  Leu  Met
               805                 810                      815

Leu  Leu  Arg  Gln  Ser  Pro  Thr  Pro  His  Gly  Leu  Ser  Leu  Ser  Asp  Leu
               820                 825                      830

Gln  Glu  Ala  Lys  Tyr  Glu  Thr  Phe  Ser  Asp  Pro  Ser  Pro  Gly  Ala
               835                 840                      845

Ile  Asp  Ser  Asn  Asn  Ser  Leu  Ser  Glu  Met  Thr  His  Phe  Arg  Pro  Gln
850                      855                      860

Leu  His  His  Ser  Gly  Asp  Met  Val  Phe  Thr  Pro  Glu  Ser  Gly  Leu  Gln
865                      870                      875                      880

Leu  Arg  Leu  Asn  Glu  Lys  Leu  Gly  Thr  Thr  Ala  Asp  Pro  Leu  Ala  Trp
               885                 890                      895

Asp  Asn  His  Tyr  Gly  Thr  Gln  Ile  Pro  Lys  Glu  Glu  Trp  Lys  Ser  Gln
               900                 905                      910

Glu  Lys  Ser  Pro  Glu  Lys  Thr  Ala  Phe  Lys  Lys  Asp  Thr  Ile  Leu
               915                 920                      925

Ser  Leu  Asn  Ala  Cys  Glu  Ser  Asn  His  Ala  Ile  Ala  Ala  Ile  Asn  Glu
930                      935                      940

Gly  Gln  Asn  Lys  Pro  Glu  Ile  Glu  Val  Thr  Trp  Ala  Lys  Gln  Gly  Arg
945                 950                      955                      960

Thr  Glu  Arg  Leu  Cys  Ser  Gln  Asn  Pro  Pro  Val  Leu  Lys  Arg  His  Gln
               965                 970                      975

Arg  Glu  Ile  Thr  Arg  Thr  Thr  Leu  Gln  Ser  Asp  Gln  Glu  Glu  Ile  Asp
               980                 985                      990

Tyr  Asp  Asp  Thr  Ile  Ser  Val  Glu  Met  Lys  Lys  Glu  Asp  Phe  Asp  Ile
          995                 1000                     1005

Tyr  Asp  Glu  Asp  Glu  Asn  Gln  Ser  Pro  Arg  Ser  Phe  Gln  Lys  Lys  Thr
          1010                     1015                     1020

Arg  His  Tyr  Phe  Ile  Ala  Ala  Val  Glu  Arg  Leu  Trp  Asp  Tyr  Gly  Met
1025                     1030                     1035                     1040

Ser  Ser  Ser  Pro  His  Val  Leu  Arg  Asn  Arg  Ala  Gln  Ser  Gly  Ser  Val
                    1045                     1050                     1055

Pro  Gln  Phe  Lys  Lys  Val  Val  Phe  Gln  Glu  Phe  Thr  Asp  Gly  Ser  Phe
               1060                     1065                     1070

Thr  Gln  Pro  Leu  Tyr  Arg  Gly  Glu  Leu  Asn  Glu  His  Leu  Gly  Leu  Leu
               1075                     1080                     1085

Gly  Pro  Tyr  Ile  Arg  Ala  Glu  Val  Glu  Asp  Asn  Ile  Met  Val  Thr  Phe
               1090                     1095                     1100

Arg  Asn  Gln  Ala  Ser  Arg  Pro  Tyr  Ser  Phe  Tyr  Ser  Ser  Leu  Ile  Ser
1105                     1110                     1115                     1120

Tyr  Glu  Glu  Asp  Gln  Arg  Gln  Gly  Ala  Glu  Pro  Arg  Lys  Asn  Phe  Val
                    1125                     1130                     1135

Lys  Pro  Asn  Glu  Thr  Lys  Thr  Tyr  Phe  Trp  Lys  Val  Gln  His  His  Met
                    1140                     1145                     1150

Ala  Pro  Thr  Lys  Asp  Glu  Phe  Asp  Cys  Lys  Ala  Trp  Ala  Tyr  Phe  Ser
                    1155                     1160                     1165

Asp  Val  Asp  Leu  Glu  Lys  Asp  Val  His  Ser  Gly  Leu  Ile  Gly  Pro  Leu
               1170                     1175                     1180

Leu  Val  Cys  His  Thr  Asn  Thr  Leu  Asn  Pro  Ala  His  Gly  Arg  Gln  Val
1185                     1190                     1195                     1200

Thr  Val  Gln  Glu  Phe  Ala  Leu  Phe  Phe  Thr  Ile  Phe  Asp  Glu  Thr  Lys
```

-continued

```
                    1205                      1210                      1215
Ser  Trp  Tyr  Phe  Thr  Glu  Asn  Met  Glu  Arg  Asn  Cys  Arg  Ala  Pro  Cys
                1220                      1225                      1230
Asn  Ile  Gln  Met  Glu  Asp  Pro  Thr  Phe  Lys  Glu  Asn  Tyr  Arg  Phe  His
                1235                      1240                      1245
Ala  Ile  Asn  Gly  Tyr  Ile  Met  Asp  Thr  Leu  Pro  Gly  Leu  Val  Met  Ala
                1250                      1255                      1260
Gln  Asp  Gln  Arg  Ile  Arg  Trp  Tyr  Leu  Leu  Ser  Met  Gly  Ser  Asn  Glu
1265                      1270                      1275                      1280
Asn  Ile  His  Ser  Ile  His  Phe  Ser  Gly  His  Val  Phe  Thr  Val  Arg  Lys
                1285                      1290                      1295
Lys  Glu  Glu  Tyr  Lys  Met  Ala  Leu  Tyr  Asn  Leu  Tyr  Pro  Gly  Val  Phe
                1300                      1305                      1310
Glu  Thr  Val  Glu  Met  Leu  Pro  Ser  Lys  Ala  Gly  Ile  Trp  Arg  Val  Glu
                1315                      1320                      1325
Cys  Leu  Ile  Gly  Glu  His  Leu  His  Ala  Gly  Met  Ser  Thr  Leu  Phe  Leu
                1330                      1335                      1340
Val  Tyr  Ser  Asn  Lys  Cys  Gln  Thr  Pro  Leu  Gly  Met  Ala  Ser  Gly  His
1345                      1350                      1355                      1360
Ile  Arg  Asp  Phe  Gln  Ile  Thr  Ala  Ser  Gly  Gln  Tyr  Gly  Gln  Trp  Ala
                1365                      1370                      1375
Pro  Lys  Leu  Ala  Arg  Leu  His  Tyr  Ser  Gly  Ser  Ile  Asn  Ala  Trp  Ser
                1380                      1385                      1390
Thr  Lys  Glu  Pro  Phe  Ser  Trp  Ile  Lys  Val  Asp  Leu  Leu  Ala  Pro  Met
                1395                      1400                      1405
Ile  Ile  His  Gly  Ile  Lys  Thr  Gln  Gly  Ala  Arg  Gln  Lys  Phe  Ser  Ser
                1410                      1415                      1420
Leu  Tyr  Ile  Ser  Gln  Phe  Ile  Ile  Met  Tyr  Ser  Leu  Asp  Gly  Lys  Lys
1425                      1430                      1435                      1440
Trp  Gln  Thr  Tyr  Arg  Gly  Asn  Ser  Thr  Gly  Thr  Leu  Met  Val  Phe  Phe
                1445                      1450                      1455
Gly  Asn  Val  Asp  Ser  Ser  Gly  Ile  Lys  His  Asn  Ile  Phe  Asn  Pro  Pro
                1460                      1465                      1470
Ile  Ile  Ala  Arg  Tyr  Ile  Arg  Leu  His  Pro  Thr  His  Tyr  Ser  Ile  Arg
                1475                      1480                      1485
Ser  Thr  Leu  Arg  Met  Glu  Leu  Met  Gly  Cys  Asp  Leu  Asn  Ser  Cys  Ser
                1490                      1495                      1500
Met  Pro  Leu  Gly  Met  Glu  Ser  Lys  Ala  Ile  Ser  Asp  Ala  Gln  Ile  Thr
1505                      1510                      1515                      1520
Ala  Ser  Ser  Tyr  Phe  Thr  Asn  Met  Phe  Ala  Thr  Trp  Ser  Pro  Ser  Lys
                1525                      1530                      1535
Ala  Arg  Leu  His  Leu  Gln  Gly  Arg  Ser  Asn  Ala  Trp  Arg  Pro  Gln  Val
                1540                      1545                      1550
Asn  Asn  Pro  Lys  Glu  Trp  Leu  Gln  Val  Asp  Phe  Gln  Lys  Thr  Met  Lys
                1555                      1560                      1565
Val  Thr  Gly  Val  Thr  Thr  Gln  Gly  Val  Lys  Ser  Leu  Leu  Thr  Ser  Met
                1570                      1575                      1580
Tyr  Val  Lys  Glu  Phe  Leu  Ile  Ser  Ser  Ser  Gln  Asp  Gly  His  Gln  Trp
1585                      1590                      1595                      1600
Thr  Leu  Phe  Phe  Gln  Asn  Gly  Lys  Val  Lys  Val  Phe  Gln  Gly  Asn  Gln
                1605                      1610                      1615
Asp  Ser  Phe  Thr  Pro  Val  Val  Asn  Ser  Leu  Asp  Pro  Pro  Leu  Leu  Thr
                1620                      1625                      1630
```

Arg Tyr Leu Arg Ile His Pro Gln Ser Trp Val His Gln Ile Ala Leu
            1635                1640                1645

Arg Met Glu Val Leu Gly Cys Glu Ala Gln Asp Leu Tyr
    1650                1655                1660

( 2 ) INFORMATION FOR SEQ ID NO:3:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

TCGACCTCCA GTTGAACATT TGTAGCAAGC CACCATGGAA ATAGAGCT					48

( 2 ) INFORMATION FOR SEQ ID NO:4:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

CTATTTCCAT GGTGGCTTGC TACAAATGTT CAACTGGAGG					40

( 2 ) INFORMATION FOR SEQ ID NO:5:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

GGGTCGACCT GCAGGCATGC CTCGAGCCGC					30

( 2 ) INFORMATION FOR SEQ ID NO:6:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

GGCCGCGGCT CGAGGCATGC CTGCAGGTCG ACCCTGCA					38

( 2 ) INFORMATION FOR SEQ ID NO:7:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

CTGAAGGTTT CTAGTTGTAT TCCAGAGGGG GAGGAG					36

( 2 ) INFORMATION FOR SEQ ID NO:8:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear (x i) SEQUENCE DESCRIPTION: SEQ ID NO:8:

GGAGAAGCTT CTTGGTTCAA TCAGACTGTC GACGATGTC    39

(2) INFORMATION FOR SEQ ID NO:9:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (x i) SEQUENCE DESCRIPTION: SEQ ID NO:9:

TCTAGCTTCA GGACTCATTG G    21

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (x i) SEQUENCE DESCRIPTION: SEQ ID NO:10:

ATACAACTAG AAACCTTCAG    20

(2) INFORMATION FOR SEQ ID NO:11:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (x i) SEQUENCE DESCRIPTION: SEQ ID NO:11:

GTAGATCAAA GAGGAAACCA G    21

(2) INFORMATION FOR SEQ ID NO:12:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (x i) SEQUENCE DESCRIPTION: SEQ ID NO:12:

GTCCCCACTG TGATGGAGC    19

(2) INFORMATION FOR SEQ ID NO:13:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (x i) SEQUENCE DESCRIPTION: SEQ ID NO:13:

AGGAAATTCC AGAGGAATAT TTGCAGAGTA AAAACAATGC CATT    44

(2) INFORMATION FOR SEQ ID NO:14:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (x i) SEQUENCE DESCRIPTION: SEQ ID NO:14:

```
AATATTCCTC  TGGAATTTCC  TCGAAATCAC  CAGTGTTCTT  GTC                                              43
```

( 2 ) INFORMATION FOR SEQ ID NO:15:

( i ) SEQUENCE CHARACTERISTICS:
        ( A ) LENGTH: 38 amino acids
        ( B ) TYPE: amino acid
        ( C ) STRANDEDNESS: single
        ( D ) TOPOLOGY: linear ( x i ) SEQUENCE DESCRIPTION: SEQ ID NO:15:

```
Val  Ser  Ser  Cys  Asp  Lys  Asn  Thr  Gly  Asp  Tyr  Tyr  Glu  Asp  Ser  Tyr
1                   5                        10                       15

Glu  Asp  Ile  Ser  Ala  Tyr  Leu  Leu  Ser  Lys  Asn  Asn  Ala  Ile  Glu  Pro
               20                       25                       30

Arg  Ser  Phe  Ser  Gln  Asn
               35
```

( 2 ) INFORMATION FOR SEQ ID NO:16:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( x i ) SEQUENCE DESCRIPTION: SEQ ID NO:16:

```
Val  Ser  Ser  Cys  Ile  Pro  Glu  Gly  Glu  Glu  Asp  Asp  Asp  Tyr  Leu  Asp
1                   5                        10                       15

Leu  Glu  Lys  Ile  Phe  Ser  Glu  Asp  Asp  Tyr  Ile  Asp  Ile  Val  Asp
               20                       25                       30

Ser  Leu  Ile  Glu  Pro  Arg  Ser  Phe  Ser  Gln  Asn
               35                  40
```

( 2 ) INFORMATION FOR SEQ ID NO:17:

( i ) SEQUENCE CHARACTERISTICS:
        ( A ) LENGTH: 34 amino acids
        ( B ) TYPE: amino acid
        ( C ) STRANDEDNESS: single
        ( D ) TOPOLOGY: linear ( x i ) SEQUENCE DESCRIPTION: SEQ ID NO:17:

```
Val  Ser  Ser  Cys  Asp  Lys  Asn  Thr  Gly  Asp  Phe  Glu  Glu  Ile  Pro  Glu
1                   5                        10                       15

Glu  Tyr  Leu  Gln  Ser  Lys  Asn  Asn  Ala  Ile  Glu  Pro  Arg  Ser  Phe  Ser
               20                       25                       30

Gln  Asn
```